(12) United States Patent
Asada et al.

(10) Patent No.: US 11,319,296 B2
(45) Date of Patent: May 3, 2022

(54) DP ANTAGONIST

(71) Applicant: ONO PHARMACEUTICAL CO., LTD., Osaka (JP)

(72) Inventors: Masaki Asada, Osaka (JP); Keisuke Hanada, Osaka (JP); Satonori Higuchi, Osaka (JP); Atsushi Naganawa, Osaka (JP); Yasuhiro Takeda, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 17/276,284

(22) PCT Filed: Sep. 19, 2019

(86) PCT No.: PCT/JP2019/036725
§ 371 (c)(1),
(2) Date: Mar. 15, 2021

(87) PCT Pub. No.: WO2020/059790
PCT Pub. Date: Mar. 26, 2020

(65) Prior Publication Data
US 2022/0033371 A1  Feb. 3, 2022

(30) Foreign Application Priority Data

Sep. 20, 2018  (JP) .............................. JP2018-175758

(51) Int. Cl.
| | |
|---|---|
| *C07D 309/06* | (2006.01) |
| *C07C 235/64* | (2006.01) |
| *C07C 233/81* | (2006.01) |
| *C07C 327/48* | (2006.01) |
| *A61P 25/20* | (2006.01) |

(52) U.S. Cl.
CPC ............ *C07D 309/06* (2013.01); *A61P 25/20* (2018.01); *C07C 233/81* (2013.01); *C07C 235/64* (2013.01); *C07C 327/48* (2013.01); *C07C 2601/14* (2017.05); *C07C 2602/08* (2017.05)

(58) Field of Classification Search
CPC ..... C07D 309/06; A61P 25/20; C07C 233/81; C07C 235/64; C07C 327/48; C07C 2601/14; C07C 2602/08
See application file for complete search history.

(56) References Cited

U.S. PATENT DOCUMENTS

| 2005/0222216 A1 | 10/2005 | Iwahashi et al. |
| 2007/0004716 A1 | 1/2007 | Naganawa et al. |

FOREIGN PATENT DOCUMENTS

| JP | S63-159342 A | 7/1988 |
| WO | WO-03/078409 A1 | 9/2003 |
| WO | WO-2005/028455 A1 | 3/2005 |
| WO | WO-2005/080367 A1 | 9/2005 |
| WO | WO-2009/022687 A1 | 2/2009 |

OTHER PUBLICATIONS

Iwahashi et al., "Design and synthesis of new prostaglandin $D_2$ receptor antagonists," Bioorganic & Medicinal Chemistry, vol. 19, Issue 18, Sep. 15, 2011, pp. 5361-5371.
Iwahashi et al., "Discovery of new orally active prostaglandin $D_2$ receptor antagonists," Bioorganic & Medicinal Chemistry, vol. 19, Issue 22, Nov. 15, 2011, pp. 6935-6948.
International Searching Authority, "International Search Report," issued in connection with International Patent Application No. PCT/JP2019/036725, dated Dec. 17, 2019.
International Searching Authority, "Written Opinion," issued in connection with International Patent Application No. PCT/JP2019/036725, dated Dec. 17, 2019.
Roberts et al., "Increased Production of Prostaglandin $D_2$ in Patients with Systemic Mastocytosis," Medical Intelligence, The New England Journal of Medicine, vol. 303, No. 24, Dec. 11, 1980, pp. 1400-1404.
Naclerio et al., "Mediator Release after Nasal Airway Challenge with Allergen$_{1-4}$," Allergenic Nasal Challenge, pp. 597-602.
Raphael et al., "The pathophysiology of rhinitis V. Sources of protein in allergen-induced nasal secretions," J. Allergy Clin. Immunol., Jul. 1991, pp. 33-42.

(Continued)

*Primary Examiner* — James D. Anderson
*Assistant Examiner* — William Y Lee
(74) *Attorney, Agent, or Firm* — Foley & Lardner LLP

(57) ABSTRACT

An object of the present invention is to provide a DP receptor antagonist. A compound represented by general formula (I):

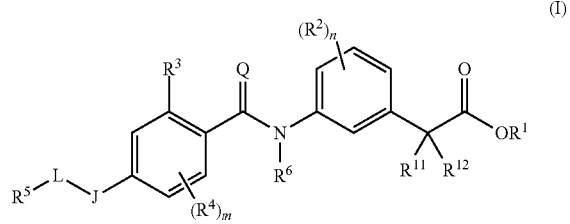

(wherein all symbols are as shown in the specification) and a pharmaceutically acceptable salt thereof have DP receptor antagonistic activity and are also highly safe, and thus are useful as active ingredients of pharmaceuticals for DP receptor-mediated diseases. In addition, the compound represented by the general formula (I) and the pharmaceutically acceptable salt thereof also have good transferability to the central nervous system, and thus are particularly useful as a preventive and/or therapeutic agent for diseases associated with DP receptors present in the central nervous system among DP receptor-mediated diseases, that is, sleep-wake disorders.

3 Claims, No Drawings

(56) References Cited

OTHER PUBLICATIONS

Brown et al., "Arachidonic Acid Metabolites During Nasal Challenge," Arch Otolaryngol Head Neck Surg, vol. 113, Feb. 1987, pp. 179-183.
Lebel et al., "Correlation between symptoms and the threshold for release of mediators in nasal secretions during nasal challenge with grass-pollen grains," J. Allergy Clin. Immunol, Nov. 1988, pp. 870-877.
Charlesworth et al., "Prednisone inhibits the appearance of inflammatory mediators and the influx of eosinophils and basophils associated with the cutaneous late-phase response to allergen," The Journal of Immunology, vol. 146, Issue 2, Jan. 1991, pp. 671-676.
Charlesworth et al., "Effect of cetirizine on mast cell-mediator release and cellular traffic during the cutaneous late-phase reaction," J. Allergy Clin. Immunol., May 1989, pp. 905-912.
Murray et al., "Release of Prostaglandin $D_2$ into Human Airways During Acute Antigen Challenge," 1 The New England Journal of Medicine, vol. 315, No. 13, Sep. 25, 1986, pp. 800-804.
Liu et al., "Evidence for Elevated Levels of Histamine, Prostaglandin $D_2$, and Other Bronchoconstricting Prostaglandins in the Airways of Subjects with Mild Asthma$_{1-3}$," Elevated Histamine and Prostaglandins in Airway Fluids in Mild Asthma, pp. 126-132.
Wenzel et al., "Bronchoalveolar lavage fluid mediator levels 5 minutes after allergen challenge in atopic subjects with asthma: Relationship to the development of late asthmatic responses," J. Allergy Clin Immunol, vol. 87, 1991, pp. 540-548.

DP ANTAGONIST

CROSS-REFERENCE TO RELATED APPLICATIONS

The present application claims priority under 37 U.S.C. § 371 to International Patent Application No. PCT/JP2019/036725, filed Sep. 19, 2019, which claims priority to and the benefit of Japanese Patent Application No. 2018-175758, filed on Sep. 20, 2018. The contents of these applications are hereby incorporated by reference in their entireties.

TECHNICAL FIELD

The present invention relates to a compound having DP receptor antagonistic activity, a pharmaceutically acceptable salt thereof, and a medicament containing them as an active ingredient. For details, a compound represented by general formula (I)

[Chemical 1]

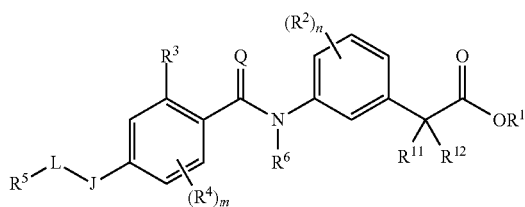

(I)

(wherein all symbols have the same meanings as described below), or a pharmaceutically acceptable salt thereof (hereinafter referred to as the compound of the present invention), and a medicament containing them as active ingredients.

BACKGROUND ART

Prostaglandin D2 (abbreviated as PGD2) is known as a metabolite of arachidonic acid cascade and is known to be involved in allergic diseases, sleep, hormone secretion, pain, platelet aggregation, glycogen metabolism, intraocular pressure regulation, and the like (Non Patent Literatures 1 to 11). It is known that DP receptors and CRTH2 receptors are present as PGD2 receptors, and it is known that, among which DP receptors that are present in the brain, especially in a subarachnoid space in a ventral region of the rostral basal forebrain, are related to a sleep-inducing action of PGD2 (Non Patent Literature 12). That is, in order to inhibit the sleep-inducing action of PGD2 and to be used as a therapeutic drug for sleep-wake disorders, it is necessary to have a drug having not only DP antagonistic activity but also transferability to the central nervous system.

On the other hand, Patent Literature 1 describes that a compound represented by the following general formula (A) that specifically binds to and antagonizes the DP receptor.

[Chemical 2]

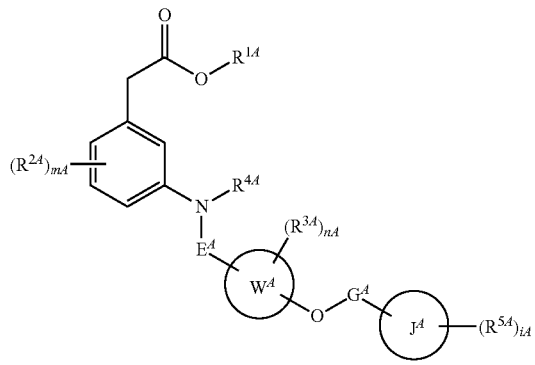

(A)

wherein $R^{1A}$ represents (1) a hydrogen atom, (2) a C1-4 alkyl group, etc., $E^A$ represents —C(=O)—, etc., $R^{2A}$ represents (1) a halogen atom, (2) a C1-6 alkyl group, etc., $R^{3A}$ represents (1) a halogen atom, 2) a C1-6 alkyl group, etc., $W^A$ represents a C5-12 monocyclic or bicyclic carbocycle, or a 5- to 12-membered monocyclic or bicyclic heterocycle, $R^{4A}$ represents (1) a hydrogen atom, (2) a C1-6 alkyl group, etc., $R^{5A}$ represents a C1-6 alkyl group, etc., (1) $G^A$ represents (1) a C1-6 alkylene group containing 0 to 2 heteroatoms selected from a nitrogen atom, an oxygen atom and a sulfur atom, $J^A$ represents a C5-12 monocyclic or bicyclic carbocycle or a 5- to 12-membered monocyclic or bicyclic heterocycle, mA represents an integer of 0 or 1 to 4, nA represents an integer of 0 or 1 to 4, and iA represents an integer of 0 or 1 to 11.

Further, Patent Literature 2 describes that a compound represented by the following general formula (B) is a compound that specifically binds to and antagonizes the DP receptor.

[Chemical 3]

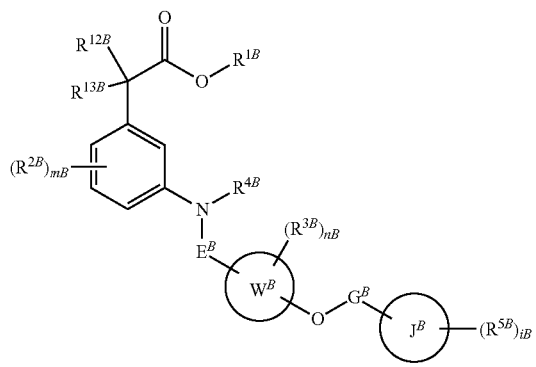

(B)

wherein $R^{1B}$ represents (1) a hydrogen atom, (2) a C1-4 alkyl group, etc., $E^B$ represents —CO— group, etc., $R^{2B}$ represents (1) a halogen atom, (2) a C1-6 alkyl group, etc., $R^{3B}$ represents (1) a halogen atom, (2) a C1-6 alkyl group, etc., $R^{4B}$ represents (1) a hydrogen atom, (2) a C1-6 alkyl group, etc., $R^{5B}$ represents a C1-6 alkyl group, etc., $W^B$ represents a C5-12 monocyclic or bicyclic carbocycle, or a 5- to 12-membered monocyclic or bicyclic heterocycle, $G^B$ represents (1) a C1-6 alkylene group containing 0 to 2 heteroatoms selected from a nitrogen atom, an oxygen atom and a sulfur atom, $J^B$ is a C5-12 monocyclic or bicyclic carbocycle or a 5- to 12-membered monocyclic or bicyclic heterocycle, mB represents an integer of 0 or 1 to 4, nB represents an integer of 0 or 1 to 4, iB represents an integer of 0 or 1 to 11, and $R^{12B}$ and $R^{13B}$ each independently represent (1) a C1-4 alkyl group that may be oxidized, (2) a hydrogen atom, etc.

However, these prior art documents do not describe or suggest anything for transferability to the central nervous system.

CITATIONS LIST

Patent Literature

Patent Literature 1: WO 2003/078409 A
Patent Literature 2: WO 2005/028455 A

Non Patent Literature

Non Patent Literature 1: The NEW ENGLAND JOURNAL of MEDICINENE, Vol. 303, 1400-1404, 1980
Non Patent Literature 2: American Review of Respiratory Disease, Vol. 128, 597-602, 1983
Non Patent Literature 3: The Journal of Allergy and Clinical Immunology, Vol. 88, 33-42, 1991
Non Patent Literature 4: Archives of Otolaryngology-Head and Neck Surgery, Vol. 113, 179-83, 1987
Non Patent Literature 5: The Journal of Allergy and Clinical Immunology, Vol. 82, 869-77, 1988
Non Patent Literature 6: The Journal of Immunology, Vol. 146, 671-676, 1991
Non Patent Literature 7: The Journal of Allergy and Clinical Immunology, Vol. 83, 905-912, 1989
Non Patent Literature 8: The NEW ENGLAND JOURNAL of MEDICINENE, Vol. 315, 800-804, 1986
Non Patent Literature 9: American Review of Respiratory Disease, Vol. 142, 126-132, 1990
Non Patent Literature 10: The Journal of Allergy and Clinical Immunology, Vol. 87, 540-548, 1991
Non Patent Literature 11: The Journal of Allergy and Clinical Immunology, Vol. 78, 458-461, 1986
Non Patent Literature 12: Proceedings of the National Academy of Sciences of the United States of America, Vol. 98, 11674-11679, 2001

SUMMARY OF INVENTION

Technical Problems

An object of the present invention is to find a compound having both strong antagonistic activity against DP receptors and good central transferability, and provide a useful compound, as a preventive and/or therapeutic agent for diseases caused by activation of DP receptor, particularly, a therapeutic agent for sleep-wake disorder.

Solutions to Problems

As a result of intensive investigations, the present inventors have found that the compound represented by general formula (I) described later solves the above-mentioned problems, and have completed the present invention by further investigations.

That is, the present invention is, in one aspect,

[1] A compound represented by general formula (I):

[Chemical 4]

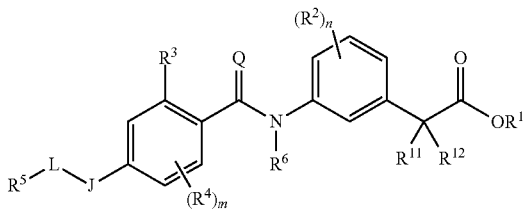

wherein $R^1$ represents a hydrogen atom, a C1-4 alkyl, or a benzyl group, $R^2$, $R^3$, and $R^4$ each independently represent (1) a halogen atom, (2) a C1-4 alkyl group optionally substituted with a halogen atom, or (3) a C1-4 alkoxy group optionally substituted with a halogen atom, when there is a plurality of each $R^2$s or $R^4$s, they may be the same or different, J represents a bond, —O—, or —S—, L represents a bond, a C1-6 alkylene, C2-6 alkenylene, or C2-6 alkynylene group, $R^5$ represents a hydrogen atom, a C3-10 carbocycle, or a 3- to 10-membered heterocycle, the C3-10 carbocycle and the 3- to 10-membered heterocycle in $R^5$ may be substituted with 1 to 6 $R^7$s, provided that when L is a bond, $R^5$ is not a hydrogen atom, $R^7$ represents (1) a halogen atom, (2) a C1-4 alkyl group optionally substituted with a halogen atom, or (3) a C1-4 alkoxy group optionally substituted with a halogen atom, when there is a plurality of $R^7$s, they may be the same or different, Q represents an oxygen atom or a sulfur atom, provided that when Q is an oxygen atom, (1) L is a C1-6 alkylene, C2-6 alkenylene, or C2-6 alkynylene group, and $R^5$ is a C3-8 monocyclic carbocycle or a 3- to 8-membered monocyclic heterocycle, or (2) L is a bond, and $R^5$ is a C3-10 carbocycle or a 3- to 10-membered heterocycle, $R^6$ represents a hydrogen atom or a C1-4 alkyl group, $R^{11}$ represents a hydrogen atom, a halogen atom, or a C1-4 alkyl group optionally substituted with a halogen atom, $R^{12}$ represents a hydrogen atom, a halogen atom, or a C1-4 alkyl group optionally substituted with a halogen atom, $R^{11}$ and $R^{12}$ may be taken together with a carbon atom to which they are attached to form a C3-6 saturated carbocycle, n represents an integer of 0 to 4, and m represents an integer of 0 to 3, or a pharmaceutically acceptable salt thereof,

[2] The compound according to [1] above, in which Q is a sulfur atom, or a pharmaceutically acceptable salt thereof,

[3] A compound according to [1] or [2] above, represented by general formula (I-1):

[Chemical 5]

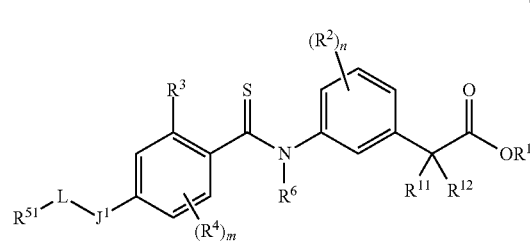

wherein R$^{51}$ represents a C3-10 carbocycle or a 3- to 10-membered heterocycle, J$^1$ represents a bond or —O—, and the other symbols have the same meanings as those described in [1] above, or a pharmaceutically acceptable salt thereof,

[4] The compound according to [3] above, in which R$^{51}$ is a C3-8 monocyclic carbocycle or a 3- to 8-membered monocyclic heterocycle, or a pharmaceutically acceptable salt thereof,

[5] The compound according to [3] above, in which R$^{51}$ is a 3- to 8-membered saturated monocyclic heterocycle, or a pharmaceutically acceptable salt thereof,

[6] The compound according to [1] above, in which Q is an oxygen atom, R$^5$ is a C3-8 monocyclic carbocycle or a 3- to 8-membered monocyclic heterocycle, or a pharmaceutically acceptable salt thereof,

[7] The compound according to [1] above, in which the compound is
(1) (4-Chloro-3-{4-[2-(oxan-2-yl)ethoxy]-2-(trifluoromethyl)benzamide}phenyl)acetic acid,
(2) {4-Chloro-3-[4-(2-cyclohexylethoxy)-2-(trifluoromethyl)benzamide]phenyl}acetic acid,
(3) {4-Chloro-3-[4-(2-phenylethoxy)-2-(trifluoromethyl)benzamide]phenyl}acetic acid,
(4) {4-Chloro-3-[4-(2-cyclopropylethoxy)-2-(trifluoromethyl)benzamide]phenyl}acetic acid,
(5) (4-Chloro-3-{2,6-dimethyl-4-[2-(oxan-2-yl)ethoxy]benzamide}phenyl)acetic acid,
(6) {4-Chloro-3-[4-(2-cyclohexylethoxy)-2,6-dimethylbenzamide]phenyl}acetic acid,
(7) {4-Chloro-3-[4-(2-cyclopropylethoxy)-2,6-dimethylbenzamide]phenyl}acetic acid,
(8) (3-{4-[(2,3-Dihydro-1H-inden-2-yl)oxy]-2,6-dimethylbenzamide}-4-fluorophenyl)acetic acid,
(9) {4-Chloro-3-[4-(3-cyclohexylprop-1-yn-1-yl)-2,6-dimethylbenzamide]phenyl}acetic acid,
(10) (4-Chloro-3-{4-[(1E)-3-cyclohexylprop-1-en-1-yl]-2,6-dimethylbenzamide}phenyl)acetic acid,
(11) (4-Chloro-3-{[4-(2-cyclohexylethoxy)-2,6-dimethylbenzene-1-carbothioyl]amino}phenyl)acetic acid,
(12) [4-Chloro-3-({4-[2-(oxan-2-yl)ethoxy]-2-(trifluoromethyl)benzene-1-carbothioyl}amino)phenyl]acetic acid,
(13) (4-Chloro-3-{[4-(2-cyclohexylethoxy)-2-(trifluoromethyl)benzene-1-carbothioyl]amino}phenyl)acetic acid,
(14) (4-Chloro-3-{[4-(2-phenylethoxy)-2-(trifluoromethyl)benzene-1-carbothioyl]amino}phenyl)acetic acid,
(15) (4-Chloro-3-{[4-(2-cyclopropylethoxy)-2-(trifluoromethyl)benzene-1-carbothioyl]amino}phenyl)acetic acid,
(16) [4-Chloro-3-({2,6-dimethyl-4-[2-(oxan-2-yl)ethoxy]benzene-1-carbothioyl}amino)phenyl]acetic acid,
(17) {4-Chloro-3-[(2,6-dimethyl-4-{2-[(2R)-oxan-2-yl]ethoxy}benzene-1-carbothioyl)amino]phenyl}acetic acid,
(18) {4-Chloro-3-[(2,6-dimethyl-4-{2-[(2S)-oxan-2-yl]ethoxy}benzene-1-carbothioyl)amino]phenyl}acetic acid,
(19) 2-{3-[({2,6-Dimethyl-4-[2-(tetrahydro-2H-pyran-2-yl)ethoxy]phenyl}carbothioyl)amino]-4-fluorophenyl}propanoic acid,
(20) 1-{3-[({2,6-Dimethyl-4-[2-(tetrahydro-2H-pyran-2-yl)ethoxy]phenyl}carbothioyl)amino]-4-fluorophenyl}cyclopropanecarboxylic acid,
(21) 2-{4-Chloro-3-[({2,6-dimethyl-4-[2-(tetrahydro-2H-pyran-2-yl)ethoxy]phenyl}carbothioyl)amino]phenyl}-2-methylpropanoic acid,
(22) 2-{4-Chloro-3-[(2,6-dimethyl-4-{2-[(2S)-oxan-2-yl]ethoxy}benzene-1-carbothioyl)amino]phenyl}-2-methylpropanoic acid,
(23) 2-{4-Chloro-3-[(2,6-dimethyl-4-{2-[(2R)-oxan-2-yl]ethoxy}benzene-1-carbothioyl)amino]phenyl}-2-methylpropanoic acid,
(24) 2-{3-[({2,6-Dimethyl-4-[2-(tetrahydro-2H-pyran-2-yl)ethoxy]phenyl}carbothioyl)amino]-4-fluorophenyl}-2-methylpropanoic acid, or
(25) 2-(4-Chloro-3-{[(2,6-dimethyl-4-{2-[(2R)-tetrahydro-2H-pyran-2-yl]ethoxy}phenyl)carbothioyl]amino}phenyl)propanoic acid, or a pharmaceutically acceptable salt thereof,

[8] A pharmaceutical composition containing the compound represented by the general formula (I), or a pharmaceutically acceptable salt thereof,

[9] The pharmaceutical composition according to [8] above, which is a DP receptor antagonist,

[10] The pharmaceutical composition according to [9] above, which is a preventive and/or therapeutic agent for a DP receptor-mediated disease,

[11] The pharmaceutical composition according to [10] above, in which the DP receptor-mediated disease is allergic disease, systemic mastocytosis, systemic mast cell activation disorder, anaphylactic shock, respiratory tract constriction, urticaria, eczema, acne, allergic bronchopulmonary aspergillosis, sinusitis, migraine, nasal polyps, hypersensitivity vasculitis, eosinophilia, contact dermatitis, a disease accompanied by itching, a disease caused secondarily as a result of behavior accompanied by itching, a disease accompanied by flushing, inflammation, chronic obstructive pulmonary disease, ischemia-reperfusion injury, cerebrovascular accident, autoimmune disease, cerebral trauma, liver disorder, graft rejection, rheumatoid arthritis, pleurisy, osteoarthritis, Crohn's disease, ulcerative colitis, irritable bowel syndrome, interstitial cystitis, muscular dystrophy, polymyositis, cancer, leukemia, viral infection, multiple sclerosis, sleep-wake disorder, or platelet aggregation,

[12] The pharmaceutical composition according to [11] above, in which the DP receptor-mediated disease is sleep-wake disorder,

[13] The pharmaceutical composition according to [12] above, in which the sleep-wake disorder is a disease based on hypersomnia, insomnia, residual sleepiness of sleep apnea syndrome, circadian rhythm sleep-wake disorder, hypersomnia associated with neurodegenerative disease, hypersomnia associated with mental illness, or morbid sleep apnea during daytime,

[14] A method for preventing and/or treating a DP receptor-mediated disease, comprising administering an effective amount of the compound represented by the general formula (I) or the pharmaceutically acceptable salt thereof according to [1] above to a mammal,

[15] The compound represented by the general formula (I) or the pharmaceutically acceptable salt thereof according to [1] above, which is used for prevention and/or treatment of a DP receptor-mediated disease,

[16] A use of the compound represented by the general formula (I) or the pharmaceutically acceptable salt thereof according to [1] above, for producing a preventive and/or therapeutic agent for a DP receptor-mediated disease,

[17] A preventive and/or therapeutic agent for a DP receptor-mediated disease containing the compound represented by the general formula (I) or the pharmaceutically acceptable salt thereof according to the above [1], and the like.

Advantageous Effects of Invention

Since the compound of the present invention has strong antagonistic activity against DP receptors and also has good central transferability, it is useful as a preventive and/or therapeutic agent for diseases caused by activation of DP receptor, particularly, a therapeutic agent for sleep-wake disorder. In addition, the compound of the present invention is excellent in safety because it selectively antagonizes a DP receptor.

DESCRIPTION OF EMBODIMENTS

Hereinafter, the present invention will be described in detail.

In the present specification, the C1-4 alkyl group includes methyl, ethyl, propyl and butyl groups, and isomers thereof.

In the present specification, the C1-4 alkoxy group includes methoxy, ethoxy, propoxy and butoxy groups, and isomers thereof.

In the present specification, examples of the C1-6 alkylene group include methylene, ethylene, propylene, butylene, pentylene, hexylene groups, and isomers thereof.

In the present specification, the C2-6 alkenylene group means, for example, a C2-6 alkenylene group having one or two double bonds, and specifically includes ethenylene, propenylene, butenylene, butadienylene, pentenylene, pentadienylene, hexenylene, hexadienylene groups, and isomers thereof.

In the present specification, the C2-6 alkynylene group means, for example, a C2-6 alkynylene group having one or two triple bonds, and specifically includes ethynylene, propynylene, butynylene, butadiynylene, pentenylene, pentadiynylene, hexenylene, hexadiynylene groups, and isomers thereof.

In the present specification, the halogen atom includes fluorine, chlorine, bromine, and iodine atoms.

In the present specification, the C3-10 carbocycle is a monocyclic or bicyclic C3-10 carbocycle, and examples thereof include cyclopropane, cyclobutane, cyclopentane, cyclopentene, cyclopentadiene, cyclohexane, cyclohexene, cyclohexadiene, benzene, cycloheptane, cycloheptene, cycloheptadiene, cyclooctane, cyclooctene, cyclooctadiene, cyclononane, cyclononene, cyclononadiene, cyclodecane, cyclodecene, pentalene, perhydropentalene, azulene, perhydroazulene, indene, perhydroindene, indane, naphthalene, dihydronaphthalene, tetrahydronaphthalene, and perhydronaphthalene rings, and the like.

In the present specification, the 3- to 10-membered heterocycle means a 3- to 10-membered monocyclic or bicyclic heterocycle containing 1 to 5 heteroatoms selected from an oxygen atom, a nitrogen atom and a sulfur atom, and examples thereof include aziridine, oxirane, thiirane, azetidine, oxetane, thietane, pyrrole, imidazole, triazole, tetrazole, pyrazole, furan, thiophene, oxazole, isooxazole, thiazole, isothiazole, furazan, oxadiazole, thiadiazole, pyrroline, pyrrolidine, imidazoline, imidazolidine, triazoline, triazolidine, tetrazoline, tetrazolidine, pyrazoline, pyrazolidine, dihydrofuran, tetrahydrofuran, dihydrothiophene, tetrahydrothiophene, dihydrooxazole, tetrahydrooxazole (oxazolidine), dihydroisoxazole, tetrahydroisoxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrothiadiazole, tetrahydrothiadiazole (thiadiazolidine), dioxolane, dithiolane, pyridine, pyrazine, pyrimidine, pyridazine, pyran, thiopyran, oxazine, oxadiazine, thiazine, thiadiazine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydropyran, tetrahydropyran, dihydrothiopyran, tetrahydrothiopyran, dihydrooxazine, tetrahydrooxazine, dihydrooxadiazine, tetrahydrooxadiazine, dihydrothiazine, tetrahydrothiazine, dihydrothiadiazine, tetrahydrothiadiazine, morpholine, thiomorpholine, oxathiane, dioxane, dithiane, azabicyclo[2.2.1]heptane, oxabicyclo[2.2.1]heptane, azabicyclo[3.1.1]heptane, azabicyclo[2.2.2]octane, diazabicyclo[2.2.2]octane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, perhydrothiadiazepine, azabicyclo[3.2.1]octane, oxabicyclo[3.2.1]octane, indole, isoindole, indolizine, benzofuran, isobenzofuran, benzothiophene, isobenzothiophene, indazole, purine, benzoxazole, benzothiazole, benzimidazole, benzofurazan, benzothiadiazole, benzotriazole, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydrobenzoxazole, perhydrobenzoxazole, dihydrobenzothiazole, perhydrobenzothiazole, dihydrobenzimidazole, perhydrobenzimidazole, dioxaindane, benzodithiolane, azaspiro[4.4]nonane, oxazaspiro[4.4]nonane, dioxaspiro[4.4]nonane, dithianaphthalene, quinoline, isoquinoline, quinolizine, phthalazine, pteridine, naphthyridine, quinoxaline, quinazoline, cinnoline, chromene, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzoxazine, dihydrobenzothiazine, pyrazinomorpholine, benzodioxane, chroman, benzodithiane, azaspiro[4.5]decane, thiaspiro[4.5]decane, dithiaspiro[4.5]decane, dioxaspiro[4.5]decane, and oxazaspiro[4.5]decane rings, and the like.

In the present specification, the C3-8 monocyclic carbocycle includes cyclopropane, cyclobutane, cyclopentane, cyclopentene, cyclopentadiene, cyclohexane, cyclohexene, cyclohexadiene, benzene, cycloheptane, cycloheptene, cycloheptadiene, cyclooctane, cyclooctene, and cyclooctadiene rings, and the like.

In the present specification, the C3-6 saturated carbocycle includes cyclopropane, cyclobutane, cyclopentane, and cyclohexane.

In the present specification, the 3- to 8-membered monocyclic heterocycle refers to a 3- to 8-membered monocyclic heterocycle containing 1 to 3 heteroatoms selected from an oxygen atom, a nitrogen atom and a sulfur atom, and examples thereof include aziridine, oxirane, thiirane, azetidine, oxetane, thietane, pyrrole, imidazole, triazole, tetrazole, pyrazole, furan, thiophene, oxazole, isoxazole, thiazole, isothiazole, furazan, oxadiazole, thiadiazole, pyrroline, pyrrolidine, imidazoline, imidazolidine, triazoline, triazolidine, tetrazoline, tetrazolidine, pyrazoline, pyrazolidine, dihydrofuran, tetrahydrofuran, dihydrothiophene, tetrahydrothiophene, dihydrooxazole, tetrahydrooxazole (oxazolidine), dihydroisoxazole, tetrahydroisoxazole (isooxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrothiadiazole, tetrahydrothiadiazole (thiadiazolidine), dioxolane, dithiolane, pyridine, pyrazine, pyrimidine, pyridazine, pyran, thiopyran, oxazine, oxadiazine, thiazine, thiadiazine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydropyran, tetrahydropyran, dihydrothiopyran, tetrahydrothiopyran, dihydrooxazine, tetrahydrooxazine, dihydrooxadiazine, tetrahydrooxadiazine, dihydrothiazine, tetrahydrothiazine, dihydrothiadiazine, tetrahydrothiadiazine, morpholine, thiomorpholine, oxathiane, dioxane, dithiane, azepine, diazepine, oxepine, thiepine, oxazepine, oxadiazepine, thiazepine, thiadiazepine, dihydroazepine, tetrahydroazepine, perhydroazepine, dihydrodiazepine, tetrahydrodiazepine, perhydrodiazepine, dihydrooxepine, tetrahydrooxepine, perhydrooxepine, dihydrothiepine, tetrahydrothiepine, perhydrothiepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine, and perhydrothiadiazepine rings, and the like.

In the present specification, the 3- to 8-membered saturated monocyclic heterocycle includes aziridine, oxirane, thiirane, azetidine, oxetane, thietane, pyrrolidine, imidazolidine, triazolidine, tetrazolidine, pyrazolidine, tetrahydrofuran, tetrahydrothiophene, tetrahydrooxazole (oxazolidine), tetrahydroisoxazole (isooxazolidine), tetrahydrothiazole (thiazolidine), tetrahydroisothiazole (isothiazolidine), tetrahydrofurazan, tetrahydrooxadiazole (oxadiazolidine), tetrahydrothiadiazole (thiadiazolidine), dioxolane, dithiolane, piperidine, piperazine, perhydropyrimidine, perhydropyridazine, tetrahydropyran, tetrahydrothiopyran, tetrahydrooxazine, tetrahydrooxadiazine, tetrahydrothiazine, tetrahydrothiadiazine, morpholine, thiomorpholine, oxathiane, dioxane, dithiane, perhydroazepine, perhydrodiazepine, perhydrooxepine, perhydrothiepine, perhydrooxazepine, perhydrooxadiazepine, perhydrothiazepine, and perhydrothiadiazepine rings, and the like.

In the present specification, a symbol

[Chemical 6]

indicates that it is attached to the other side of a paper (that is, α-configuration), a symbol

[Chemical 7]

indicates that it is attached to the front side of a paper (that is, β-configuration), and a symbol

[Chemical 8]

indicates an α-configuration, a β-configuration, or a mixture thereof in any proportion.

Among the compounds represented by the general formula (I), preferred embodiments are, for example, compounds represented by General formula (I-a):

[Chemical 9]

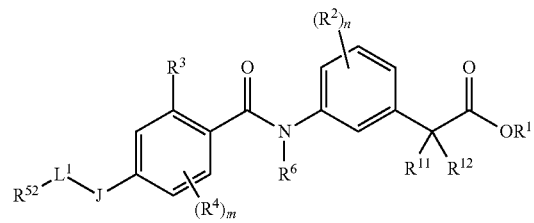

(I-a)

(wherein $L^1$ represents a C1-6 alkylene, C2-6 alkenylene, or C2-6 alkynylene group, $R^{52}$ represents a C3-8 monocyclic carbocycle or a 3- to 8-membered monocyclic heterocycle, and other symbols have the same meanings as described above), and pharmaceutically acceptable salts thereof, other preferred embodiments are compounds represented by general formula (I-b):

[Chemical 10]

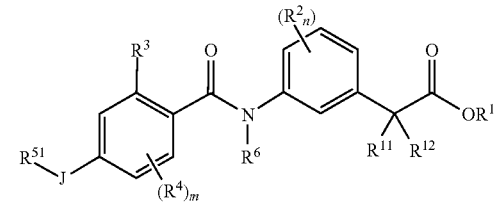

(I-b)

(wherein all symbols have the same meanings as described above), and pharmaceutically acceptable salts thereof, and particularly preferred embodiments are compounds represented by general formula (I-c-0):

[Chemical 11]

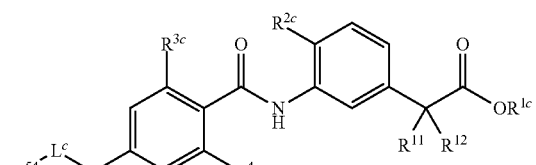

(I-c-0)

(wherein $R^{1c}$ is a hydrogen atom or a methyl group, $R^{2c}$ is a fluorine atom or a chlorine atom, $R^{3c}$ is a methyl group or a trifluoromethyl group, and $R^{4c}$ is a hydrogen atom, a methyl group, or a trifluoromethyl group, and when -$L^c$-$J^c$- is —O—, $R^{54}$ is

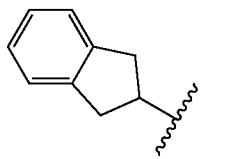

or when -L$^c$-J$^c$- is

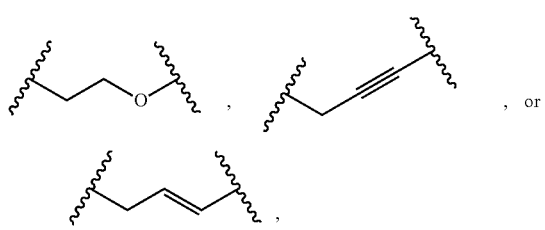, or

R$^{54}$ is

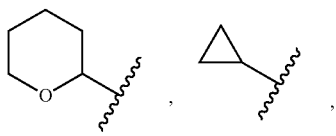

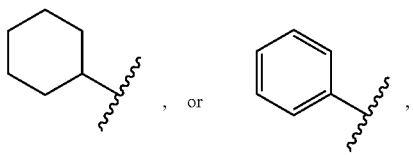, or and other symbols have the same meanings as described above), and pharmaceutically acceptable salts thereof.

Other particularly preferred embodiments are compounds represented by general formula (I-c):

[Chemical 15]

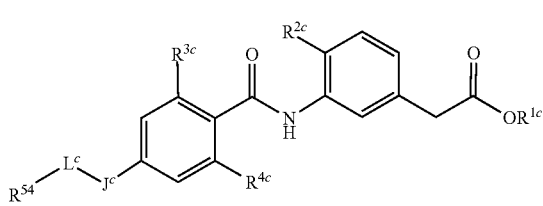

(I-c)

(wherein all symbols have the same meanings as described above), and pharmaceutically acceptable salts thereof.

In the general formula (I), other preferred embodiments are compounds represented by general formula (I-d):

[Chemical 16]

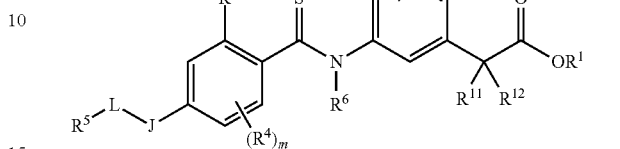

(I-d)

(wherein all symbols have the same meanings as described above), and pharmaceutically acceptable salts thereof. More preferred embodiments are compounds represented by general formula (I-1):

[Chemical 17]

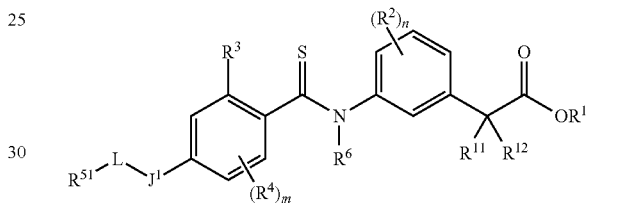

(I-1)

(wherein all symbols have the same meanings as described above) and pharmaceutically acceptable salts thereof, and further preferred embodiments are compounds represented by general formula (I-2-0):

[Chemical 18]

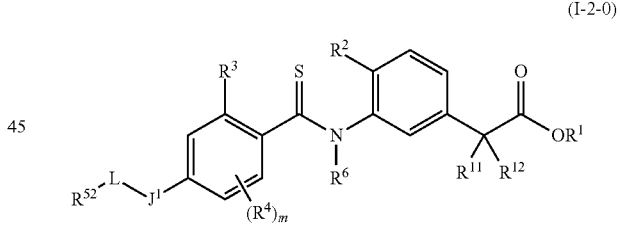

(I-2-0)

(wherein all symbols have the same meanings as described above) and pharmaceutically acceptable salts thereof, and other further preferred embodiments are compounds represented by general formula (I-2):

[Chemical 19]

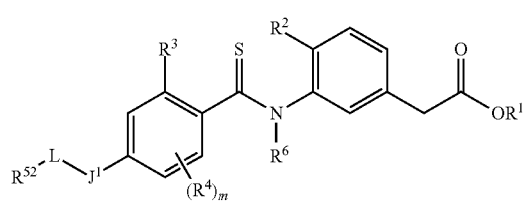

(I-2)

(wherein all symbols have the same meanings as described above), and pharmaceutically acceptable salts thereof. Most preferred embodiments are compounds represented by general formula (I-3-0):

[Chemical 20]

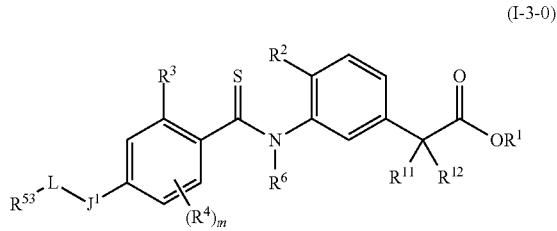

(I-3-0)

(wherein $R^{53}$ is a 3- to 8-membered saturated monocyclic heterocycle, and other symbols have the same meanings as described above), and pharmaceutically acceptable salts thereof. Other most preferred embodiments are compounds represented by general formula (I-3):

[Chemical 21]

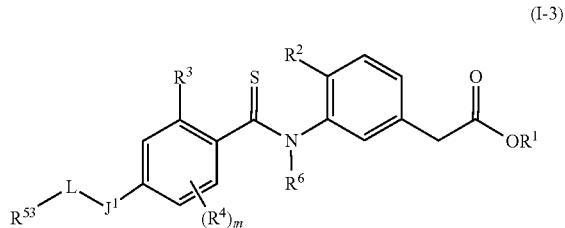

(I-3)

(wherein all symbols have the same meanings as described above), and pharmaceutically acceptable salts thereof.

Alternatively, most preferred embodiments are compounds represented by general formula (I-4):

[Chemical 22]

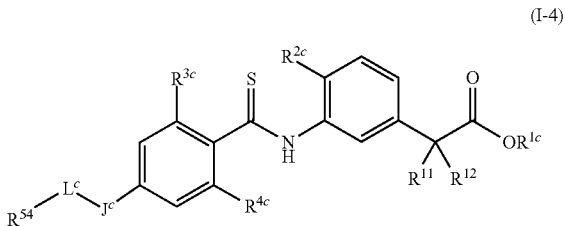

(I-4)

(wherein all symbols have the same meanings as described above), and pharmaceutically acceptable salts thereof.

In any of the general formulae (I), (I-a), (I-b), (I-d), (I-1), (I-2-0), (I-2), (I-3-0), and (I-3), $R^1$ is preferably a hydrogen atom or a C1-4 alkyl group, more preferably a hydrogen atom or a methyl group, and particularly preferably a hydrogen atom.

Also, in any of the general formulae (I-c-0), (I-c) and (1-4), $R^{1c}$ is preferably a hydrogen atom.

In any of the general formulae (I), (I-a), (I-b), (I-d), (I-1), (I-2-0), (I-2), (I-3-0), and (I-3), $R^2$ is preferably a halogen atom, more preferably a fluorine atom or a chlorine atom, and particularly preferably a chlorine atom.

Also, in any of the general formulae (I-c-0), (I-c) and (1-4), $R^{2c}$ is preferably a chlorine atom.

In any of the general formulae (I), (I-a), (I-b), (I-d), (I-1), (I-2-0), (I-2), (I-3-0), and (I-3), $R^3$ is preferably a C1-4 alkyl group which may be substituted with a halogen atom, and particularly preferably a methyl group or a trifluoromethyl group.

In any of the general formulae (I), (I-a), (I-b), (I-d), (I-1), (I-2-0), (I-2), (I-3-0), and (I-3), $R^4$ is preferably a C1-4 alkyl group which may be substituted with a halogen atom, more preferably a methyl group or a trifluoromethyl group, and particularly preferably a methyl group.

In the general formula (I-c-0), (I-c), or (I-4), $R^{4c}$ is preferably a hydrogen atom or a methyl group.

Also, in any of the general formulae (I), (I-a), (I-b), and (I-d), J is preferably a bond or —O—, and more preferably —O—.

In any of the general formulae (I-1), (I-2-0), (I-2), (I-3-0), and (I-3), $J^1$ is preferably —O—.

In the general formula (I) or (I-d), $R^5$ is preferably a C3-10 carbocycle or a 3- to 10-membered heterocycle, more preferably a C3-8 monocyclic carbocycle or a 3- to 8-membered monocyclic heterocycle, and further preferably a 3- to 8-membered saturated monocyclic heterocycle. Alternatively, in the general formula (I) or (I-d), $R^5$ is preferably a cyclopropane, cyclobutane, cyclopentane, cyclohexane, benzene, or a tetrahydropyran ring, further preferably a cyclohexane, benzene, cyclopropane, or tetrahydropyran ring, and most preferably a tetrahydropyran ring. Further, the preferable $R^5$ may be substituted with (preferably 1 to 3) $R^7$.

In the general formula (I-b) or (I-1), $R^{51}$ is preferably a C3-8 monocyclic carbocycle or a 3- to 8-membered monocyclic heterocycle, and more preferably a 3- to 8-membered saturated monocyclic heterocycle. Alternatively, in the general formula (I-b) or (I-1), $R^{51}$ is preferably a cyclopropane, cyclobutane, cyclopentane, cyclohexane, benzene, or tetrahydropyran ring, further preferably a cyclohexane, benzene, cyclopropane, or tetrahydropyran ring, and most preferably a tetrahydropyran ring.

In the general formula (I-a), (I-2-0), or (I-2), $R^{52}$ is preferably a 3- to 8-membered saturated monocyclic heterocycle. Alternatively, in the general formula (I-a), (I-2-0), or (I-2), $R^{52}$ is preferably a cyclopropane, cyclobutane, cyclopentane, cyclohexane, benzene, or tetrahydropyran ring, more preferably a cyclopropane, cyclohexane, benzene, or tetrahydropyran ring, and most preferably a tetrahydropyran ring.

In the general formula (I-3-0) or (I-3), $R^{53}$ is preferably a tetrahydropyran ring.

In the general formula (I-c-0), (I-c) or (1-4), $R^{54}$ is preferably a tetrahydropyran ring.

In the general formula (I), Q is preferably a sulfur atom.

In any of the general formulae (I), (I-d), (I-1), (I-2-0), (I-2), (I-3-0), and (I-3), L is preferably a C1-6 alkylene, C2-6 alkenylene, or C2-6 alkynylene group, further preferably ethylene, propenylene, or propynylene, and more preferably an ethylene group.

In the general formula (I-a), $L^1$ is preferably ethylene, propenylene, or propynylene, and more preferably an ethylene group.

In the general formula (I), (I-a), (I-d), (I-1), (I-2-0), (I-2), (I-3-0), or (I-3), -L-J-, -$L^1$-J- or -L-$J^1$- is preferably —O—,

[Chemical 23]

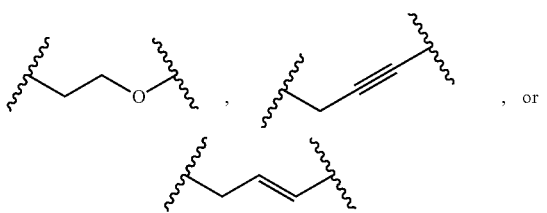

and more preferably

[Chemical 24]

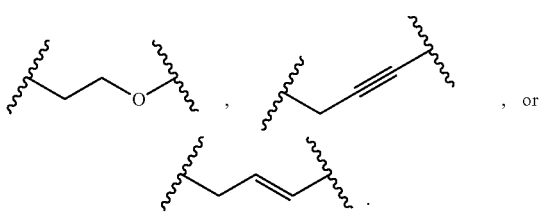

In any of the general formulae (I), (I-a), (I-b), (I-d), (I-1), (I-2-0), (I-2), (I-3-0), and (I-3), $R^6$ is preferably a hydrogen atom.

In any of the general formulae (I), (I-a), (I-b), (I-c), (I-d), (I-1), (I-2-0), (I-3-0), and (I-4), $R^{11}$ is preferably a hydrogen atom, a methyl group, or an ethyl group, more preferably a hydrogen atom or a methyl group, and most preferably a hydrogen atom.

In any of the general formulae (I), (I-a), (I-b), (I-c), (I-d), (I-1), (I-2-0), (I-3-0), and (I-4), $R^{12}$ is preferably a hydrogen atom, a methyl group, or an ethyl group, more preferably a hydrogen atom or a methyl group, and most preferably a hydrogen atom.

In any of the general formulae (I), (I-a), (I-b), (I-c), (I-d), (I-1), (I-2), (I-3), and (I-4), $R^{11}$ and $R^{12}$ may be taken together with the carbon atoms to which they are attached to form a C3-6 saturated carbocycle, and the C3- to 6-membered saturated carbocycle is preferably a cyclopropane ring.

In any of the general formulae (I), (I-a), (I-b), (I-d), and (I-1), n is preferably 1.

In any of the general formulae (I), (I-a), (I-b), (I-d), (I-1), (I-2-0), (I-2), (I-3-0), and (I-3), m is preferably 0 or 1, and more preferably 1.

As the compound represented by the general formula (I), compounds in which some or all of the above-mentioned preferable $R^1$, $R^2$, $R^3$, $R^4$, $R^5$, $R^6$, $R^{11}$, $R^{12}$, J, L, Q, n and m are combined are preferable.

As the compound represented by the general formula (I-a), compounds in which some or all of the above-mentioned preferable $R^1$, $R^2$, $R^3$, $R^4$, $R^{52}$, $R^6$, $R^{11}$, $R^{12}$, J, $L^1$, n and m are combined are preferable.

As the compound represented by the general formula (I-b), compounds in which some or all of the above-mentioned preferable $R^1$, $R^2$, $R^3$, $R^4$, $R^{51}$, $R^6$, $R^{11}$, $R^{12}$, J, n and m are combined are preferable.

As the compound represented by the general formula (I-c-0), compounds in which some or all of the above-mentioned preferable $R^{1c}$, $R^{2c}$, $R^{3c}$, $R^{4c}$, $R^{11}$, $R^{12}$, $J^c$, $L^c$, and $R^{54}$ are combined are preferable.

As the compound represented by the general formula (I-c), compounds in which some or all of the above-mentioned preferable $R^{1c}$, $R^{2c}$, $R^{3c}$, $R^{4c}$, $J^c$, $L^c$, and $R^{54}$ are combined are preferable.

As the compound represented by the general formula (I-d), compounds in which some or all of the above-mentioned preferable $R^1$, $R^2$, $R^3$, $R^4$, $R^5$, $R^6$, $R^{11}$, $R^{12}$, J, L, n and m are combined are preferable.

As the compound represented by the general formula (I-1), compounds in which some or all of the above-mentioned preferable $R^1$, $R^2$, $R^3$, $R^4$, $R^{51}$, $R^6$, $R^{11}$, $R^{12}$, $J^1$, L, n and m are combined are preferable.

As the compound represented by the general formula (I-2-0), compounds in which some or all of the above-mentioned preferable $R^1$, $R^2$, $R^3$, $R^4$, $R^{52}$, $R^6$, $R^{11}$, $R^{12}$, $J^1$, L, and m are combined are preferable.

As the compound represented by the general formula (I-2), compounds in which some or all of the above-mentioned preferable $R^1$, $R^2$, $R^3$, $R^4$, $R^{52}$, $R^6$, $J^1$, L, and m are combined are preferable.

As the compound represented by the general formula (I-3-0), compounds in which some or all of the above-mentioned preferable $R^1$, $R^2$, $R^3$, $R^4$, $R^{53}$, $R^6$, $R^{11}$, $R^{12}$, $J^1$, L, and m are combined are preferable.

As the compound represented by the general formula (I-3), compounds in which some or all of the above-mentioned preferable $R^1$, $R^2$, $R^3$, $R^4$, $R^{53}$, $R^6$, $J^1$, L, and m are combined are preferable.

As the compound represented by the general formula (I-4), compounds in which some or all of the above-mentioned preferable $R^{1c}$, $R^{2c}$, $R^{3c}$, $R^{4c}$, $J^c$, $L^c$, $R^{11}$, $R^{12}$, and $R^{54}$ are combined are preferable.

In the present specification, another embodiment of the general formula (I) is most preferably a compound of the present invention described in the examples below, or a pharmaceutically acceptable salt thereof.

[Isomer]

In the present invention, unless otherwise noted, isomers are all encompassed. For example, alkyl groups, alkoxy groups, alkylene groups and the like include straight-chain and branched ones. Furthermore, isomers (E, Z, cis, trans isomers) in a double bond, ring or condensed ring, isomers due to the presence of asymmetric carbon or the like (R-, S-form, α-, β-configuration, enantiomers, diastereomers), optically active substances with racemic properties (D, L, d, l-forms), polar compounds obtained by chromatographic separation (high-polarity compounds, low-polarity compounds), equilibrium compounds, rotational isomers, and mixtures in any proportion and racemic mixtures thereof in any proportion are all encompassed by the present invention. Moreover, in the present invention, all isomers due to tautomerism are also included.

In the present invention, all references to the compound of the present invention include the compounds represented by the general formula (I), pharmaceutically acceptable salts thereof, N-oxides thereof, solvates thereof, or co-crystals thereof.

[Salt]

The compound represented by the general formula (I) is converted into a salt by a known method.

The salt is a pharmaceutically acceptable salt.

The salt is preferably water-soluble.

Examples of the pharmaceutically acceptable salt include acid addition salts, alkali metal salts, alkaline earth metal salts, ammonium salts, amine salts, and the like.

Examples of the acid addition salts include inorganic acid salts such as hydrochlorides, hydrobromides, hydroiodides, sulfates, phosphates and nitrate, and organic acid salts such as acetates, lactates, tartrates, benzoates, citrates, methanesulfonates, ethanesulfonates, trifluoroacetates, benzenesulfonates, toluenesulfonates, isethionates, glucuronates and gluconates.

Examples of the alkali metal salt include potassium salts, sodium salts, and the like.

Examples of the alkaline earth metal salt include calcium salts, magnesium salts, and the like.

Examples of the ammonium salt include tetramethylammonium salts and the like.

Examples of the amine salt include triethylamine salts, methylamine salts, dimethylamine salts, cyclopentylamine salts, benzylamine salts, phenethylamine salts, piperidine salts, monoethanolamine salts, diethanolamine salts, tris(hydroxymethyl)aminomethane salts, lysine salts, arginine salts, N-methyl-D-glucamine salts, and the like.

[N-Oxide]

The compound represented by the general formula (I) can be converted into an N-oxide by any method. The N-oxide represents a compound in which the nitrogen atom of the compound represented by the general formula (I) is oxidized. The N-oxide of the compound represented by the general formula (I) may be a salt.

[Solvate]

The compound represented by the general formula (I), the pharmaceutically acceptable salt thereof, and the N-oxide thereof may exist in an unsolvated form or may exist in a solvated form with a pharmaceutically acceptable solvent such as water or ethanol. The compound represented by the general formula (I), the pharmaceutically acceptable salt thereof, and the N-oxide thereof can be converted into a solvate by a known method.

The solvate is preferably non-toxic and water-soluble. Examples of a suitable solvate include solvates like hydrates or alcoholic solvents (for example, ethanol, etc.).

[Co-Crystal]

The compound represented by the general formula (I), the pharmaceutically acceptable salt thereof, and the N-oxide thereof can form co-crystals with a suitable co-crystal forming agent. The co-crystal forming agent is preferably one that is pharmaceutically acceptable. A co-crystal is typically defined as a crystal in which two or more different molecules are formed by intermolecular interactions that differ from ionic bonds. Further, the co-crystal may be a complex of a neutral molecule and a salt. The co-crystal can be adjusted by known methods, such as by melt crystallization, by recrystallization from a solvent, or by physically pulverizing a component together. Suitable co-crystal forming agent includes those described in WO 2006/007448 A.

[Prodrug]

The compound represented by the general formula (I) can be administered as a prodrug. A prodrug of the compound represented by the general formula (I) refers to a compound that is converted into the compound represented by the general formula (I) by a reaction with an enzyme, gastric acid or the like in vivo. Examples of the prodrug of the compound represented by the general formula (I) include, when the compound represented by the general formula (I) has a carboxy group, compounds in which the carboxy group is esterified or amidated (for example, compounds in which the carboxy group of the compound represented by the general formula (I) is ethyl esterified, phenyl esterified, carboxymethyl esterified, dimethylaminomethyl esterified, pivaloyloxymethyl esterified, 1-{(ethoxycarbonyl)oxy}ethyl esterified, phtalidyl esterified, (5-methyl-2-oxo-1,3-dioxolen-4-yl)methyl esterified, 1-{[(cyclohexyloxy)carbonyl]oxy}ethyl esterified, methylamidated, etc.) and the like. These compounds can be produced by a method known per se. In addition, the prodrug of the compound represented by the general formula (I) may be changed to the compound represented by the general formula (I) under physiological conditions described in "Development of Drug" published in 1990 by Hirokawa Shoten, Vol. 7, "Molecular Design", pp. 163-198. The prodrug of the compound represented by the general formula (I) may be a salt or a solvate, or may form a co-crystal with a suitable co-crystal forming agent.

[Labeled Compound]

The compound of the present invention also includes so-called labeled compounds in which some or all of the atoms constituting them are replaced by their isotopes. These labeled compounds can be produced by a method known per se. As isotopes used for labeling, for example, $^2H$, $^3H$, $^{11}C$, $^{13}C$, $^{14}C$, $^{13}N$, $^{15}N$, $^{17}O$, $^{18}O$, $^{18}F$, $^{35}S$, $^{36}Cl$, $^{77}Br$, $^{125}I$ and the like can be suitably used, but are not limited thereto.

[Method for Producing Compound of Present Invention]

The compound of the present invention represented by the general formula (I) can be produced by a known method, for example, a method described in Comprehensive Organic Transformations: A Guide to Functional Group Preparations, 2nd Edition (Richard C. Larock, John Wiley & Sons Inc, 2018), a method shown below, a method equivalent to these, or a method shown in Examples. In each of the following production methods, a raw material compound may be used as a salt. As such a salt, those described as pharmaceutically acceptable salts of the compound of the present invention represented by the general formula (I) are preferable.

Among the compounds represented by the general formula (I), a compound in which $R^1$ is a hydrogen atom, J is —O— or —S—, and Q is an oxygen atom, that is, the compound represented by the general formula (Ia):

[Chemical 25]

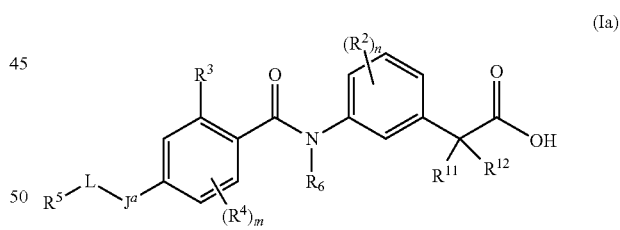

(Ia)

(wherein P represents —O— or —S—, and the other symbols have the same meaning as above.)

can be produced according to a following reaction step formula A.

Reaction step Chemical A

[Chemical 26]

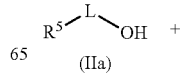

(IIa)

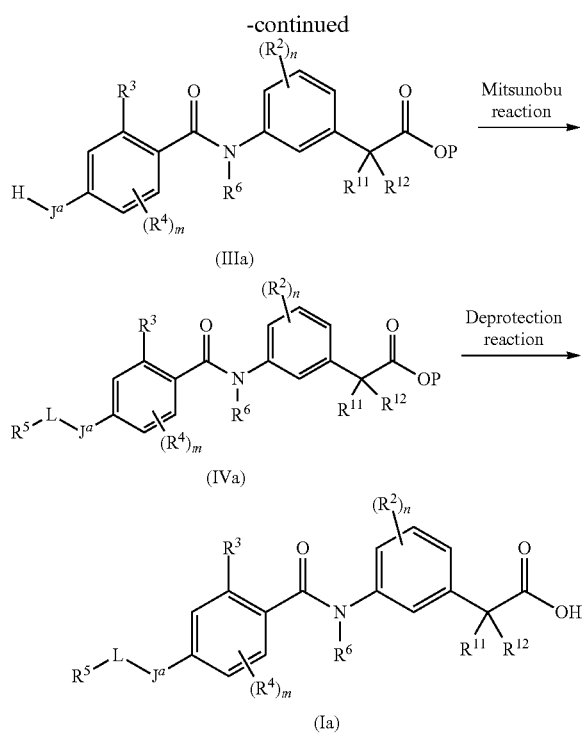

(wherein P represents a protecting group for a carboxy group, and other symbols have the same meanings as described above)

That is, a compound represented by general formula (IIa) and a compound represented by general formula (IIIa) are subjected to Mitsunobu reaction to produce a compound represented by general formula (IVa), and then a deprotection reaction of a carboxy group is carried out, whereby the compound represented by the general formula (Ia) can be produced.

The Mitsunobu reaction is known, and is performed by, for example, reacting an alcohol with a phenol derivative or a thiophenol derivative at 0 to 60° C. in an organic solvent (dichloromethane, diethyl ether, tetrahydrofuran, acetonitrile, benzene, toluene, etc.) in the presence of combination of a Mitsunobu reagent (diazo compound (diethyl azodicarboxylic acid (DEAD), diisopropyl azodicarboxylate, 1,1'-(azodicarbonyl)dipiperidine, 1,1'-azobis(N,N-dimethylformamide), etc.) and a phosphine compound (triphenylphosphine, tributylphosphine, trimethylphosphine, polymer support triphenylphosphine, etc.), or an ylide reagent (cyanomethylene trimethylphosphorane (CMMP), cyanomethylene tributylphosphorane (CMBP), etc.).

The compound represented by the general formula (IVa) can be also produced by subjecting a compound represented by general formula (Va):

[Chemical 57]

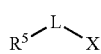

(Va)

(wherein X represents a leaving group such as a halogen atom, a tosyloxy group (TsO—) or a mesyloxy group (MsO—), and other symbols have the same meanings as described above) and the compound represented by the general formula (IIIa) to an alkylation reaction.

This alkylation reaction is known and is carried out by reacting at 0 to 100° C., for example, in an organic solvent (dimethylformamide, dimethylsulfoxide, chloroform, dichloromethane, diethyl ether, tetrahydrofuran, methyl t-butyl ether, etc.), in the presence of an alkali metal hydroxide (sodium hydroxide, potassium hydroxide, lithium hydroxide, etc.), an alkali earth metal hydroxide (barium hydroxide, calcium hydroxide, etc.) or a carbonate (sodium carbonate, potassium carbonate, etc.) or an aqueous solution thereof, or a mixture thereof.

In the reaction step formula A, the deprotection reaction of a carboxy group is known and can be carried out as follows.

Examples of the protecting group for a carboxy group include a methyl group, an ethyl group, an allyl group, a t-butyl group, a trichloroethyl group, a benzyl (Bn) group, a phenacyl group, and the like. The protecting group for a carboxy group is not particularly limited as long as it is a group that can be easily and selectively desorbed other than those described above. For example, those described in Peter G. M. Wuts, Green's Protective Groups in Organic Synthesis, Fifth Edition, Wiley, New York, 2014 are used.

Deprotection reaction of a carboxy group is well known, and examples thereof include:

(1) alkaline hydrolysis,
(2) deprotection reaction under acidic conditions,
(3) deprotection reaction by hydrogenolysis,
(4) deprotection reaction of a silyl group,
(5) deprotection reaction using a metal,
(6) deprotection reaction using a metal complex, and the like.

These methods are specifically described hereinbelow.

(1) Deprotection reaction by alkaline hydrolysis is carried out, for example, in an organic solvent (methanol, tetrahydrofuran, dioxane, etc.), by using an alkali metal hydroxide (sodium hydroxide, potassium hydroxide, lithium hydroxide, etc.), an alkaline earth metal hydroxide (barium hydroxide, calcium hydroxide, etc.) or a carbonate (sodium carbonate, potassium carbonate, etc.) or an aqueous solution thereof or a mixture thereof at a temperature of 0 to 60° C.

(2) Deprotection reaction under acidic conditions is carried out, for example, in an organic solvent (dichloromethane, chloroform, dioxane, ethyl acetate, anisole, etc.), in an organic acid (acetic acid, trifluoroacetic acid, methanesulfonic acid, p-tosyl acid, etc.) or an inorganic acid (hydrochloric acid, sulfuric acid, etc.) or a mixture thereof (hydrogen bromide/acetic acid, etc.) at a temperature of 0 to 100° C.

(3) Deprotection reaction by hydrogenolysis is carried out, for example, in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitriles (acetonitrile, etc.), amides (dimethylformamide, etc.), water, ethyl acetate, acetic acid or mixed solvents of two or more of thereof, etc.), in the presence of a catalyst (palladium-carbon, palladium black, palladium hydroxide, platinum oxide, Raney nickel, etc.), in a hydrogen atmosphere of normal or increased pressure or in the presence of ammonium formate at a temperature of 0 to 200° C.

(4) Deprotection reaction of a silyl group is carried out, for example, in a water-miscible organic solvent (tetrahydrofuran, acetonitrile, etc.), by using tetrabutylammonium fluoride at a temperature of 0 to 40° C.

(5) Deprotection reaction using a metal is carried out, for example, in an acidic solvent (acetic acid, a buffer of pH 4.2 to 7.2 or a mixed solution thereof with an organic solvent such as tetrahydrofuran), in the presence of zinc powder, with application of ultrasonic if necessary, at a temperature of 0 to 40° C.

(6) Deprotection reaction using a metal complex is carried out, for example, in an organic solvent (dichloromethane, dimethylformamide, tetrahydrofuran, ethyl acetate, acetonitrile, dioxane, ethanol, etc.), water or a mixed solvent thereof, in the presence of a trap reagent (tributyltin hydride, triethylsilane, dimedone, morpholine, diethylamine, pyrrolidine, etc.), in the presence of an organic acid (acetic acid, formic acid, 2-ethylhexanoic acid, etc.) and/or a salt of an organic acid (sodium 2-ethylhexanoate, potassium 2-ethylhexanoate, etc.), in the presence or absence of a phosphine reagent (triphenylphosphine, etc.), by using a metal complex (tetrakistriphenylphosphine palladium(0), bis(triphenylphosphine)palladium(II) dichloride, palladium(II) acetate, tris(triphenylphosphine)rhodium(I) chloride, etc.) at a temperature of 0 to 40° C.

In addition to the above, the deprotection reaction can be carried out by the method described in, for example, Peter G. M. Wuts, Green's Protective Groups in Organic Synthesis, Fifth Edition, Wiley, New York, 2014.

As can be easily understood by those skilled in the art, the target compound of the present invention can be easily produced by properly using these deprotection reactions.

Among the compounds represented by the general formula (I), a compound in which $R^1$ is a hydrogen atom, Q is an oxygen atom, J is a bond, and L is an alkynylene group, that is, a compound represented by general formula (Ib):

[Chemical 28]

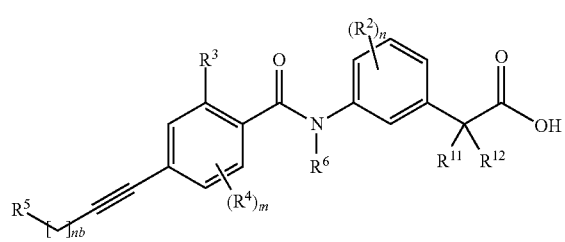

(Ib)

(wherein nb represents an integer of 0 to 4, and other symbols have the same meaning as above)

can be produced by subjecting a compound represented by general formula (IIIb):

[Chemical 29]

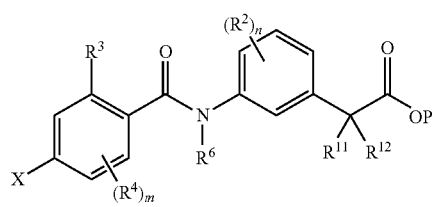

(IIIb)

(wherein X represents a halogen atom or a trifluoromethanesulfonyloxy group (TfO—), and other symbols have the same meanings as described above) and a compound represented by general formula (Vb):

[Chemical 30]

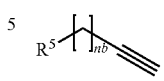

(Vb)

(wherein all symbols have the same meaning as above)

to a coupling reaction, and then carrying out a deprotection reaction of carboxy groups. This coupling reaction is known, and the compound can be produced by reacting the compound represented by the general formula (IIIb) and the compound represented by the general formula (Vb), for example, in an organic solvent (for example, tetrahydrofuran, N,N-dimethylformamide, acetonitrile, etc.), in the presence of a palladium catalyst (bistriphenylphosphine palladium(II) chloride, etc.), in the presence of a copper catalyst (copper iodide(I), etc.), and in the presence of a base (triethylamine, etc.), at room temperature to reflux temperature.

Among the compounds represented by the general formula (I), a compound in which $R^1$ is a hydrogen atom, Q is an oxygen atom, J is a bond, and L is an alkenylene or an alkylene group can be produced by subjecting the compound represented by the general formula (Tb) to a reduction reaction.

The reduction reaction is known, and carried out, for example, in a hydrogen atmosphere, in an organic solvent (for example, methanol, ethanol, ethyl acetate, tetrahydrofuran, acetic acid, 1,2-dimethoxyethane, or a solvent obtained by appropriately mixing these organic solvents, etc.) or a mixed solvent of the organic solvents and water, in the presence of a palladium catalyst (for example, palladium-carbon, palladium hydroxide, Lindlar's catalyst, etc.) at a temperature of room temperature to about 80° C.

Among the compounds represented by the general formula (I), a compound in which $R^1$ is a hydrogen atom and Q is a sulfur atom, that is, a compound represented by general formula (Ic):

[Chemical 31]

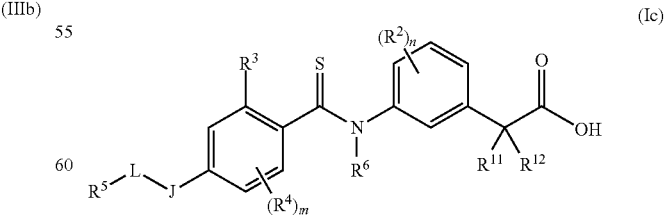

(Ic)

(wherein all symbols have the same meanings as described above) can be produced according to a following reaction step formula C.

Reaction step Chemical C

[Chemical 32]

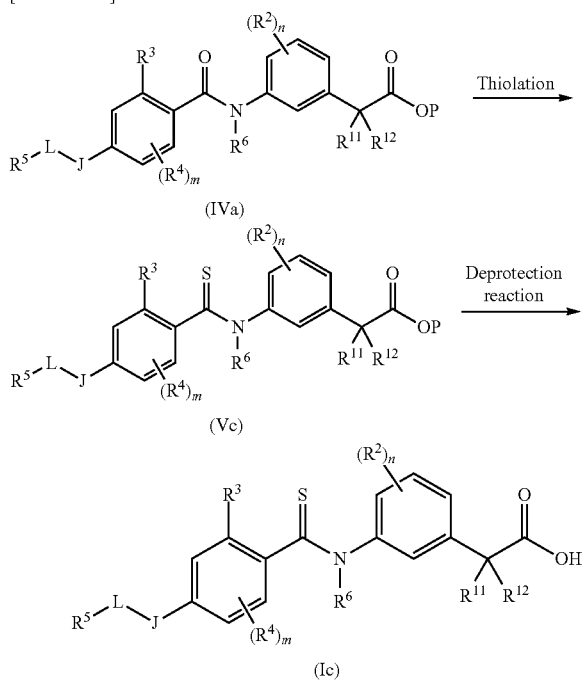

(wherein all symbols have the same meaning as above)

That is, the compound represented by the general formula (IVa) is subjected to a thiolation reaction to produce a compound represented by general formula (Vc), and then a deprotection reaction of a carboxy group is carried out, whereby the compound represented by the general formula (Ic) can be produced.

In the reaction step formula C, the thiolation reaction is known, and the compound can be produced by reacting an amide compound in an organic solvent (for example, tetrahydrofuran, toluene, benzene, acetonitrile, dichloromethane, pyridine, etc.), in the presence or absence of a base (sodium bicarbonate, etc.), in the presence or absence of a thiolation reagent (for example, Lawesson's reagent (2,4-bis(4-methoxyphenyl)-1,3,2,4-dithiadiphosphetane-2,4-disulfide), tetraphosphorus decasulfide, diphosphorus pentasulfide, hydrogen sulfide, sulfur, etc.) and a phosphine reagent (for example, trichlorophosphate, etc.) at room temperature to reflux temperature.

In each of the above reactions, the compound used as a starting material is known or can be easily produced by a known method.

For example, the compound represented by the general formula (IIIa):

[Chemical 33]

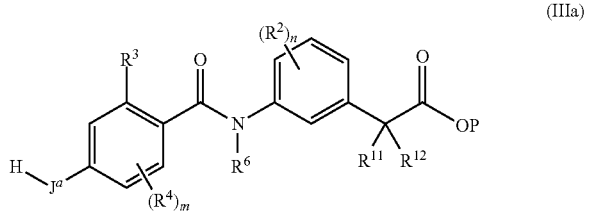

(wherein all symbols have the same meanings as described above) can be produced by carrying out a protection/deprotection reaction as necessary according to a following reaction step formula D.

Reaction step Chemical D

[Chemical 34]

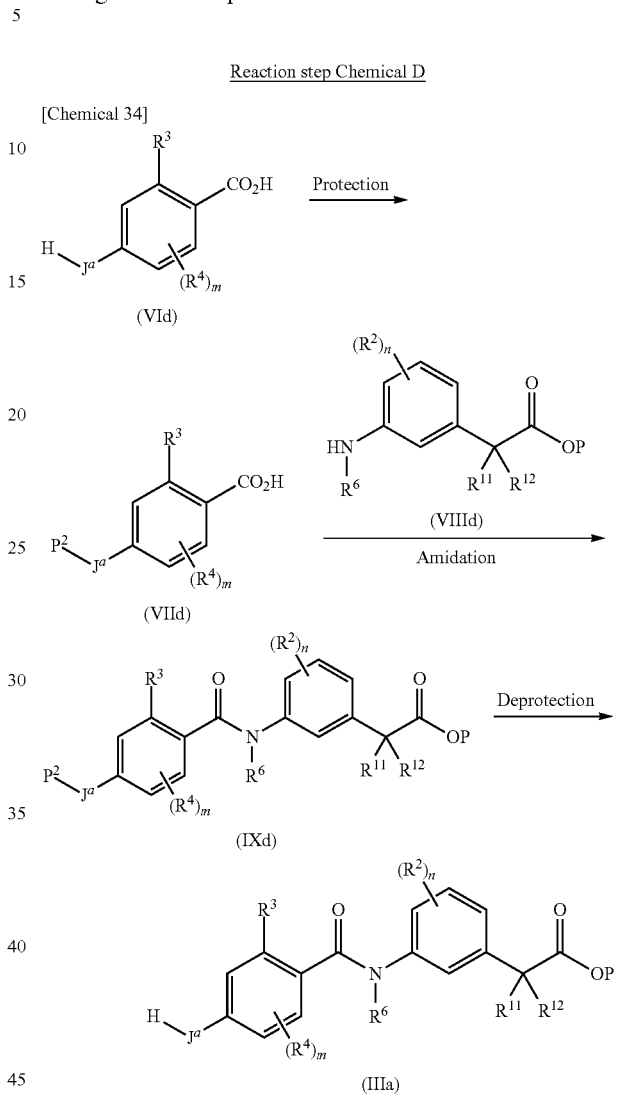

(wherein $P^2$ represents a protecting group for a hydroxyl group or a thiol group, and other symbols have the same meanings as described above)

That is, a compound represented by general formula (VId) is subjected to a protection reaction of a hydroxyl group or a thiol group to produce a compound represented by general formula (VIId), and then subjected to an amidation reaction with a compound represented by general formula (VIIId), whereby a compound represented by general formula (IXd) can be produced. Then, the compound represented by the general formula (IXd) is subjected to a deprotection reaction of a hydroxyl group or a thiol group, whereby the compound represented by the general formula (IIIa) can be produced.

Examples of the protecting group for a hydroxyl group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group, and the like.

Examples of the protecting group for a thiol group include a benzyl group, a methoxybenzyl group, a methoxymethyl (MOM) group, a 2-tetrahydropyranyl (THP) group, a diphenylmethyl group, and an acetyl (Ac) group.

The protecting group for a hydroxyl group or a thiol group is not particularly limited as long as it is a group that can be easily and selectively desorbed other than those described above. For example, those described in Peter G. M. Wuts, Green's Protective Groups in Organic Synthesis, Fifth Edition, Wiley, New York, 2014 are used.

In the reaction step formula D, the amidation reaction is known, and examples thereof include:
(1) a method using an acid halide,
(2) a method using a mixed acid anhydride,
(3) a method using a condensing agent, and the like.

These methods are specifically described hereinbelow.

(1) The method using an acid halide is carried out, for example, by reacting carboxylic acid with an acid halogenating agent (oxalyl chloride, thionyl chloride, etc.) in an organic solvent (chloroform, dichloromethane, diethylether, tetrahydrofuran, etc.) or in the absence of a solvent at −20° C. to reflux temperature, and reacting the obtained acid halide with amine in the presence of a base (pyridine, triethylamine, dimethylaniline, dimethylaminopyridine, diisopropylethylamine, etc.) in an organic solvent (chloroform, dichloromethane, diethylether, tetrahydrofuran, etc.) at a temperature of 0 to 80° C. Alternatively, it can also be carried out by reacting the obtained acid halide with amine in an organic solvent (dioxane, tetrahydrofuran, etc.) using an alkaline aqueous solution (sodium bicarbonate solution, sodium hydroxide solution, etc.) at 0 to 40° C.

(2) The method using a mixed acid anhydride is carried out, for example, by reacting carboxylic acid with an acid halide (pivaloyl chloride, tosyl chloride, mesyl chloride, etc.) or an acid derivative (ethyl chloroformate, isobutyl chloroformate, etc.) at 0 to 40° C. in the presence of a base (pyridine, triethylamine, dimethylaniline, dimethylaminopyridine, diisopropylethylamine, etc.) in an organic solvent (chloroform, dichloromethane, diethylether, tetrahydrofuran, etc.) or in the absence of a solvent, and reacting the obtained mixed acid anhydride with amine at 0 to 40° C. in an organic solvent (chloroform, dichloromethane, diethylether, tetrahydrofuran, etc.).

(3) The method using a condensing agent is carried out, for example, by reacting carboxylic acid with amine in an organic solvent (chloroform, dichloromethane, dimethyl formamide, diethylether, tetrahydrofuran, etc.) or in the absence of a solvent at 0 to 80° C. in the presence or absence of a base (pyridine, triethylamine, dimethylaniline, dimethylaminopyridine, etc.), using a condensing agent (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, 1-propylphosphonic acid cyclic anhydride (1-propanephosphonic acid cyclic anhydride, $T_3P$), etc.) in the presence or absence of 1-hydroxybenztriazole (HOBt).

It is desirable that all of the reactions (1), (2) and (3) be carried out under an atmosphere of an inert gas (argon, nitrogen, etc.) under anhydrous conditions.

The deprotection reaction of a hydroxyl group or a thiol group in the reaction step formula D is known and can be carried out in the same manner as the deprotection reaction of a carboxy group in the reaction step formula A.

As can be easily understood by those skilled in the art, the target compound of the present invention can be easily produced by properly using these deprotection reactions.

Compounds used as other starting materials and compounds used as reagents are known per se or can be easily produced by using methods in combination with a known method, for example, a method described in Comprehensive Organic Transformations: A Guide to Functional Group Preparations, 2nd Edition (Richard C. Larock, John Wiley & Sons Inc, 2018) or the like.

In the reactions in the present specification, each group may be protected when protection is required, and the compound protected by a protecting group can be appropriately subjected to a known deprotection reaction.

In the reactions in the present specification, reactions involving heating can be carried out, as apparent to those skilled in the art, using a water bath, an oil bath, a sand bath or a microwave.

In the reactions in the present specification, a solid phase supported reagent which is supported on a high molecular polymer (for example, polystyrene, polyacrylamide, polypropylene, polyethylene glycol, etc.) may be used.

In the reactions in the present specification, reaction products can be purified according to a conventional purification means such as distillation at normal or reduced pressure, high performance liquid chromatography using silica gel, magnesium silicate or the like, thin layer chromatography, ion exchange resins, scavenger resins or column chromatography or washing and re-crystallization. Purification may be carried out after each reaction or after a few reactions.

[Toxicity]

The compound of the present invention has very low toxicity and is safe enough for use as a medicament.

[Application to Pharmaceuticals]

Since the compound of the present invention has excellent DP receptor antagonistic activity, it is useful for the DP receptor-mediated disease, for example, allergic disease, systemic mastocytosis, systemic mast cell activation disorder, anaphylactic shock, respiratory tract constriction, urticaria, eczema, acne, allergic bronchopulmonary aspergillosis, sinusitis, migraine, nasal polyps, hypersensitivity vasculitis, eosinophilia, contact dermatitis, a disease accompanied by itching, a disease caused secondarily as a result of behavior accompanied by itching, a disease accompanied by flushing, inflammation, chronic obstructive pulmonary disease, ischemia-reperfusion injury, cerebrovascular accident, autoimmune disease, cerebral trauma, liver disorder, graft rejection, rheumatoid arthritis, pleurisy, osteoarthritis, Crohn's disease, ulcerative colitis, irritable bowel syndrome, interstitial cystitis, muscular dystrophy, polymyositis, cancer, leukemia, viral infection, multiple sclerosis, sleep-wake disorder, or platelet aggregation. Furthermore, since the compound of the present invention has excellent transferability to the central nervous system, it is particularly useful for sleep-wake disorder, for example, hypersomnia (for example, narcolepsy, sudden hypersomnia, recurrent hypersomnia, and Kleine-Levin syndrome, etc.), insomnia, residual sleepiness of sleep apnea syndrome, circadian rhythm sleep-wake disorder (for example, shift work circadian rhythm disorder, irregular sleep-wake rhythm disorder, etc.), hypersomnia associated with neurodegenerative disease (for example, Parkinson's disease, Lewy body dementia, and Alzheimer's dementia, etc.), hypersomnia associated with mental illness (for example, depression, and bipolar disorder, etc.), and morbid sleep apnea during daytime.

The compound of the present invention may be combined with another drug so as to be administered as a concomitant drug in order to:

1) complement and/or enhance a preventive and/or therapeutic effect of the compound;
2) improve kinetics and uptake and reduce dose of the compound; and/or
3) decrease side effect of the compound.

The concomitant drug of the compound of the present invention and another drug may be administered in the form of a combined agent containing both components in one preparation or may be administered in the form of separate preparations. When administered as separate preparations, simultaneous administration and staggered administration are included. Further, for staggered administration, the compound of the present invention may be administered first and another drug may be administered later, or another drug may be administered first and the compound of the present invention may be administered later. Each administration method may be the same or different.

The disease on which a preventive and/or therapeutic effect is exerted by the concomitant drug is not particularly limited, and any disease that complements and/or enhances the preventive and/or therapeutic effect of the compound of the present invention may be used.

Examples of another drug for complementing and/or enhancing the preventive and/or therapeutic effect on sleep-wake disorders of the compounds of the present invention include psychostimulants (for example, modafinil, methylphenidate (hydrochloride), methamphetamine (hydrochloride), pemoline, etc.), narcolepsy therapeutics (for example, γ-hydroxybutyric acid, clomipramine, etc.), acetylcholine esterase inhibitors (for example, donepezil (hydrochloride), physostigmine, rivastigmine (tartrate), galantamine (hydrobromide), zanapezil (fumarate); TAK-147, tacrine, metrifonate, etc.), NMDA receptor antagonists (for example, ketamine, memantine, dextromethorphan hydrobromide, etc.), dopamine receptor agonists (for example, levodopa, bromocriptine, pergolide, talipexole, pramipexole (hydrochloride) (hydrate), cabergoline, amantadine (hydrochloride), etc.), tricyclic antidepressants (for example, amitriptyline hydrochloride, imipramine hydrochloride, etc.), selective serotonin reuptake inhibitors (for example, paroxetine, escitalopram, etc.), mania treatments (for example, lithium carbonate, etc.), antipsychotics (for example, clofekton, spiperone, sulpiride, zotepine, timiperone, haloperidol decanoate, fluphenazine decanoate, haloperidol, pimozide, propericiazine, bromperidol, perphenazine, levomepromazine maleate, chlorpromazine hydrochloride, thioridazine hydrochloride, trazodone hydrochloride, mosapramine hydrochloride, risperidone, olanzapine, etc.), noradrenaline reuptake inhibitors (for example, atomoxetine, etc.), and the like.

The mass ratio of the compound of the present invention to another drug is not particularly limited.

Another drug may be administered in combination of any two or more types.

In addition, another agent that complements and/or enhances the preventive and/or therapeutic effect of the compound of the present invention include those which have so far been found based on the above mechanism but also those which will be found in the future.

In order to use the compound of the present invention as a single agent or in combination with another agent as a concomitant drug, for the purpose of prevention and/or treatment of the above diseases, the substance as an active ingredient is usually formulated with various additives or a pharmaceutically acceptable carrier such as a solvent and then administered systemically or topically in oral or parenteral form. Here, the pharmaceutically acceptable carrier means a substance other than the active ingredient, which is generally used in the preparation of pharmaceuticals. The pharmaceutically acceptable carrier preferably has no pharmacological action at a dose of the preparation, is harmless, and does not interfere with the therapeutic effect of the active ingredient. In addition, the pharmaceutically acceptable carrier can also be used for the purpose of enhancing usefulness of the active ingredient and the preparation, facilitating the formulation, stabilizing quality, improving usability, or the like. Specifically, substances such as those described in "Encyclopedia of Pharmaceutical Additives" (edited by International Pharmaceutical Excipients Council Japan) published in 2016 by Yakuji Nippo, Limited may be appropriately selected according to the purpose.

Examples of a dosage form used for administration include preparations for oral administration (e.g., tablets, capsules, granules, powders, liquids and solutions for oral administration, syrups, jellies for oral administration, etc.), preparations for oro-mucosal application (e.g., tablets for oro-mucosal application, sprays for oro-mucosal application, semi-solid preparations for oro-mucosal application, preparations for gargles, etc.), preparations for injection (e.g. injections, etc.), preparations for dialysis (e.g. dialysis agents, etc.), preparations for inhalation (e.g., inhalants, etc.), preparations for ophthalmic application (e.g. ophthalmic liquids and solutions, ophthalmic ointments, etc.), preparations for otic application (e.g. ear preparations, etc.), preparations for nasal application (e.g. nasal preparations, etc.), preparations for rectal application (e.g. suppositories for rectal application, semi-solid preparations for rectal application, enemas for rectal application, etc.), preparations for vaginal application (e.g. tablets for vaginal use, suppositories for vaginal use, etc.), preparations for cutaneous application (e.g. solid preparations for cutaneous application, liquids and solutions for cutaneous application, sprays for cutaneous application, ointments, creams, gels, patches, etc.), and the like.

[Preparations for Oral Administration]

Examples of the preparations for oral administration include tablets, capsules, granules, powders, liquids and solutions for oral administration, syrups, jellies for oral administration, and the like. In addition, preparations for oral administration include fast-disintegrating preparations in which release of active ingredient(s) from the preparation is not particularly adjusted, and release-controlled preparations in which release is adjusted according to the purpose by a unique formulation design and manufacturing method, for example, enteric-coated preparations, sustained-release preparations, and the like. The enteric-coated preparation refers to a preparation designed so that active ingredient(s) is not released in stomach but mainly in small intestine for the purpose of preventing decomposition of the active ingredient(s) in the stomach or reducing an irritating effect of the active ingredient(s) on the stomach, and can be usually produced by applying a film using an acid-insoluble enteric base. The sustained-release preparation refers to a preparation in which a release rate, release time, and release site of active ingredient(s) from the preparation are adjusted for the purpose of reducing the number of administrations, reducing side effects or the like, and can be usually produced by using an appropriate sustained-release agent. Of the preparations for oral administration, capsules, granules, tablets, etc. can be also coated with appropriate coating agents such as sugars, sugar alcohols or polymer compounds, for the purpose of facilitating administration or preventing decomposition of the active ingredient.

(1) Tablets

Tablets are solid preparations having a certain shape and size, intended for oral administration, and intraoral quickly disintegrating tablets, chewable tablets, effervescent tablets, dispersible tablets, soluble tablets and the like are included besides those generally called tablets such as uncoated tablets, film-coated tablets, sugar-coated tablets, multi-layered tablets, and dry-coated tablets. Uncoated tables are usually produced using the following method (a), (b) or (c):

(a) Mix homogeneously active ingredient(s) with additives such as excipients, binders and disintegrants, granulate the mixture with water or a solution containing a binder by an appropriate method, then mix with a lubricant and the like, and compression-mold the mixture;

(b) Mix homogeneously active ingredient(s) with additives such as excipients, binders and disintegrants, and directly compression-mold the mixture, or mix homogeneously granules previously prepared with additives with active ingredient(s), a lubricant and the like, and then compression-mold the mixture; and (c) Mix homogeneously active ingredient(s) with additives such as excipients and binders, pour the kneaded product moistened with a solvent into a certain mold for molding, and then dry the molded product by an appropriate method.

Film-coated tablets can be usually produced by coating uncoated tablets with thin films using appropriate coating agents such as polymer compounds. Sugar-coated tablets can be usually produced by coating uncoated tablets using coating agents including sugars or sugar alcohols. Multi-layer tablets can be produced by stacking particulates having different compositions in layers and compression-molding them by an appropriate method. Dry-coated tablets can be produced by covering inner core tablets with outer layers having different compositions. In addition, tablets can be also prepared as enteric coated tablets or sustained-release tablets using an appropriate known method. Intraoral quickly disintegrating tablets, chewable tablets, effervescent tablets, dispersible tablets and soluble tablets are tablets that have been given unique functions by appropriate selection of additives, and can be produced according to the method for producing tablets described above. Intraoral quickly disintegrating tablets refer to tablets that can be quickly dissolved or disintegrated in the oral cavity and taken; chewable tablets refer to tablets that are chewed and taken; effervescent tablets refer to tablets that are dissolved or dispersed while rapidly bubble in water; dispersible tablets refer to tablets that are dispersed in water and taken; and soluble tablets refer to tablets that are dissolved in water and taken. Effervescent tablets can be produced by using an appropriate acidic substance, carbonate, hydrogen carbonate or the like as additives.

(2) Capsules

Capsules are preparations filled in capsules or encapsulation-molded with capsule bases, and hard capsules, soft capsules and the like are included. Hard capsules can be produced by a method where a homogeneous mixture obtained by mixing active ingredient(s) with additives such as excipients, or granules or molded product obtained by an appropriate method, are filled into capsule as they are or after slightly molding. Soft capsules can be produced by a method where a mixture obtained by adding additives to active ingredient(s) is encapsulation-molded in a certain shape with appropriate capsule bases such as gelatin plasticized by addition of glycerin, D-sorbitol, or the like. Capsules can be prepared as enteric-coated capsules or sustained-release capsules using an appropriate known method, and a coloring agent, a preservative or the like can also be added to the capsule base.

(3) Granules

Granules are preparations granulated into granules, and effervescent granules and the like are included besides those generally called granules. Granules are usually produced using the following method (a), (b) or (c):

(a) Mix homogeneously powdered active ingredient(s) with an excipient, a binder, a disintegrant or other additives, and then granulate the mixture by an appropriate method;

(b) Mix homogeneously active ingredient(s) previously prepared in granules with additives such as excipients; and (c) Mix active ingredient(s) previously prepared in granules with additives such as excipients, and granulate the mixture by an appropriate method.

Granules can be also coated if necessary, and can be also prepared as enteric-coated granules or sustained-release granules using an appropriate known method. Effervescent granules can be produced by using an appropriate acidic substance, carbonate, hydrogen carbonate or the like as additives. The effervescent granules refer to granules that are dissolved or dispersed while rapidly bubble in water. Granules can be also prepared as fine granules by adjusting particle size.

(4) Powders

Powders are preparations in powder form, and can be usually produced by mixing homogeneously active ingredient(s) with an excipient or other additives.

(5) Liquids and Solutions for Oral Administration

Liquids and solutions for oral administration are liquid, or flowable, viscous and gelatinous preparations, and elixirs, suspensions, emulsions and lemonades and the like are included besides those generally called oral solutions. Liquids and solutions for oral administration can be usually produced by mixing active ingredient(s) with additives and purified water, homogeneously dissolving, emulsifying or suspending the mixture, and filtering the mixture if necessary. Elixirs refer to clear, sweetened and aromatic liquids and solutions for oral administration in liquid form containing ethanol, and can be usually produced by adding ethanol, purified water, an aromatic agent and sucrose, other sugars or sweetening agents to solid active ingredient(s) or exudate thereof and dissolving them, and clarifying the solution by filtration or other methods. Suspensions refer to liquids and solutions for oral administration of active ingredient(s) finely and homogeneously suspended, and can be usually produced by adding a suspending agent or other additives and purified water or oil to a solid active ingredient(s) and suspending them by an appropriate method to homogenize the entire suspension. Emulsions refer to liquids and solutions for oral administration of active ingredient(s) finely and homogeneously emulsified, and can be usually produced by adding an emulsifying agent and purified water to liquid active ingredient(s) and emulsifying them by an appropriate method to homogenize the entire suspension. In addition, lemonades refer to sweet and sour, clear liquids and solutions for oral administration in liquid form.

(6) Syrups

Syrups are viscous liquid or solid preparations containing sugars or sweetening agents, and preparations for syrups and the like are included. Syrups can be usually produced by adding active ingredient(s) to a solution of syrup, other sugars or sweetening agents, or a simple syrup, and dissolving, mixing, suspending or emulsifying them, and if necessary, boiling and then filtering the mixture while hot. Preparations for syrups refer to preparations in form of granules or powders, which become syrups by adding water, and they may be also termed dry syrups. Preparations for syrups can be usually produced by using sugars or sweetening agents as additives, according to the production method of granules or powders.

(7) Jellies for Oral Administration

Jellies for oral administration are non-flowable molded gelatinous preparations, and can be usually produced by mixing active ingredient(s) with additives and a polymer gel base, and gelatinizing and molding the mixture into a certain shape by an appropriate method.

[Preparations for Injection]

(1) Injections

Injections are sterile preparations to be administered subcutaneously, intramuscularly, intraarticularly, or directly into body tissues or organs such as blood vessels, in form of a solution, a suspension or an emulsion, or of a solid to be dissolved or suspended before use, and freeze-dried injections, powders for injections, prefilled syringes for injections, cartridges for injections, parenteral infusions, implants/pellets, prolonged-release injections and the like are included. Injections are usually produced using the following method (a) or (b):

(a) Dissolve, suspend or emulsify homogeneously active ingredient(s) as it is or added with additives in water for injection, other aqueous solvent or non-aqueous solvent or the like, fill the mixture into a container for injection, seal, and sterilize; and (b) Dissolve, suspend or emulsify homogeneously active ingredient(s) as it is or added with additives in water for injection, other aqueous solvent or non-aqueous solvent or the like and filtrate aseptically the mixture, or prepare aseptically a homogeneous liquid, fill the mixture into a container for injection, and seal.

Freeze-dried Injections can be usually produced by dissolving active ingredient(s) as it is or active ingredient(s) with additives such as excipients in water for injection, filtrate aseptically the solution, filling the filtrate into a container for injection and then being freeze-dried, or freeze-drying the filtrate in special containers and then filling it into individual containers for injection. Powders for injections can be usually produced by filtrating aseptically active ingredient(s), adding powders obtained by crystallization or the powders added with sterilized additives, and filling the powders into a container for injection. Prefilled syringes for injections can be usually produced by filling into syringes active ingredient(s) as it is or a solution, suspension, or emulsion prepared using active ingredient(s) and additives. Cartridges for injections refer to injections used by fixing a cartridge filled with a chemical solution in an injector for exclusive use. The cartridge filled with a chemical solution can be usually produced by filling into a cartridge active ingredient(s) as it is or a solution, suspension, or emulsion prepared using active ingredient(s) and additives. Parenteral infusions usually refer to injections of 100 mL or more, intended for intravenous administration. Implants/pellets refer to solid or gel-like injections applied subcutaneously, intramuscularly, etc. using an implant device or by means of operative treatment, for the purpose of releasing active ingredient(s) for a long period of time. Implants/pellets can be usually produced in a form of pellet, microsphere or gel using biodegradable polymer compounds. Prolonged-release injections refer to injections to be applied intramuscularly or intraarticularly, for the purpose of releasing active ingredient(s) for a long period of time, and can be usually produced by dissolving or suspending active ingredient(s) in vegetable oil or the like, or by preparing a suspension of microspheres using biodegradable polymer compounds.

A dose of the compound of the present invention or a concomitant drug of the compound of the present invention and another drug varies depending on an age, a weight, symptom, a therapeutic effect, an administration method, a treatment time, and the like. However, the compound of the present invention or a concomitant drug of the compound of the present invention and another drug is administered orally, usually, in a range of 1 ng to 1000 mg per once per adult, once to several times a day, or is administered parenterally, in a range of 0.1 ng to 100 mg per once per adult, once to several times a day, or continuously administered intravenously, in a range of 1 to 24 hours a day. As described above, since the dose varies depending on various conditions, a dose smaller than the above dose may be sufficient, or administration beyond the range may be necessary.

Unless otherwise defined, all technical terms, scientific terms and the abbreviated terms used herein have the same meaning as commonly understood by one of ordinary skill in the art to which this invention belongs.

In addition, contents of all patent literatures and non patent literatures or references explicitly cited herein may be entirely incorporated herein as a part of the present specification.

EXAMPLES

Hereinafter, the present invention will be described in detail with reference to Examples, but the present invention is not limited thereto.

Synthesis Example

Solvents in parentheses shown in chromatographic separation part and TLC indicate used elution solvents or development solvents, and the proportion represents a volume ratio.

A solvent in parentheses shown in NMR part indicates a solvent used in measurement.

The compound names used in this specification were named using a computer program that names generally according to IUPAC rules, ACD/Name (registered trademark), or Chemdraw Ultra (version 12.0, manufactured by Cambridge Soft), or named according to IUPAC nomenclature.

LC-MS/ELSD was carried out under the following conditions.

Column: Waters Triart $C_{18}$ (particle diameter: $1.9 \times 10^{-6}$ m; column length: $30 \times 2.0$ mm I.D.); flow rate: 1.0 mL/min; column temperature: 30° C.; mobile phase (A): 0.1% trifluoroacetic acid aqueous solution; mobile phase (B): 0.1% trifluoroacetic acid-acetonitrile solution; gradient (the ratio of mobile phase (A):mobile phase (B)): [0 min] 95:5; [0.1 min]95:5; [1.2 min] 5:95; [1.4 min] 5:95; [1.41 min] 95:5; [1.5 min] 95:5; detectors: UV (PDA), ELSD, MS.

HPLC Retention time indicates a retention time under the conditions described in the LC-MS/ELSD unless otherwise specified.

Supercritical fluid chromatography (SFC) was carried out under the following conditions.

Column: CHIRALPAK IC/SFC (Daicel Corporation), inner diameter 20 mm×length 250 mm, particle diameter 5

µm; flow rate: 100 mL/min: Co-solvent/CO$_2$=12/88: ISOCRATIC 21 min (Co-solvent: MeCN/MeOH=9/1); Back-pressure: 120 bar.

Reference Example 1: 4-(Acetoxy)-2-(trifluoromethyl)benzoic Acid

Pyridine (0.392 mL) and acetic anhydride (0.573 mL) were added to a solution of 4-hydroxy-2-(trifluoromethyl)benzoic acid (CAS. No. 320-32-1, 500 mg) in ethyl acetate (7.5 mL), and the mixture was stirred overnight. Water and dilute hydrochloric acid were added to the reaction mixture, then the mixture was extracted with ethyl acetate. The organic layer was washed with water and saturated saline solution, dried over sodium sulfate, and then concentrated under reduced pressure to obtain a title compound (528 mg) having following physical property values.

$^1$H-NMR (DMSO-d$_6$): δ 2.34, 7.56, 7.70, 7.91, 13.66.

Reference Example 2: 4-(Chlorocarbonyl)-3-(trifluoromethyl)phenyl Acetate

Thionyl chloride (0.17 mL) was added to a toluene (1.6 mL)-acetonitrile (0.26 mL) solution of the compound (1.0 g) produced in Reference Example 1, and the mixture was stirred at 60° C. for 4 hours. A compound obtained by concentrating the reaction solution under reduced pressure was used for a next reaction without purification.

Reference Example 3: Methyl{3-[4-(acetoxy)-2-(trifluoromethyl)benzamide]-4-chlorophenyl}acetate Pyridine (0.342 mL) and methyl 2-(3-amino-4-chlorophenyl)acetate (CAS. No. 59833-69-1, 422 mg) was added to a toluene (1.6 mL)-acetonitrile (1.6 mL) solution of the compound produced in Reference Example 2, and the mixture was stirred overnight at room temperature. Water was added to the reaction mixture, and the mixture was extracted with ethyl acetate. The organic layer was washed successively with 1 mol/L hydrochloric acid, water and saturated saline solution, dried over sodium sulfate, and then concentrated under reduced pressure. The obtained residue was purified by silica gel column chromatography (hexane:ethyl acetate=70:30) to obtain a title compound (715 mg) having following physical property values.

$^1$H-NMR (CDCl$_3$): δ 2.37, 3.68, 3.72, 7.07, 7.37, 7.43, 7.53, 7.71, 7.93, 8.45.

Reference Example 4: Methyl{4-chloro-3-[4-hydroxy-2-(trifluoromethyl)benzamide]phenyl}acetate Potassium carbonate (404 mg) was added to a solution of the compound (1.75 g) produced in Reference Example 3 in methanol (8.8 mL)-tetrahydrofuran (8.8 mL), and the mixture was stirred at room temperature for 2 hours. Water and 1 mol/L hydrochloric acid were added to the reaction mixture, then the mixture was extracted with ethyl acetate. The organic layer was washed with water and saturated saline solution, dried over sodium sulfate, and then concentrated under reduced pressure to obtain a title compound (1.36 g) having following physical property values.

TLC: Rf 0.55 (hexane:ethyl acetate=1:1);

$^1$H-NMR (CDCl$_3$): δ 3.63, 3.75, 7.12-7.16, 7.19, 7.49, 7.52, 7.59, 10.07, 10.52.

Example 1: Methyl(4-chloro-3-{4-[2-(oxan-2-yl)ethoxy]-2-(trifluoromethyl)benzamide}phenyl)acetate

[Chemical 35]

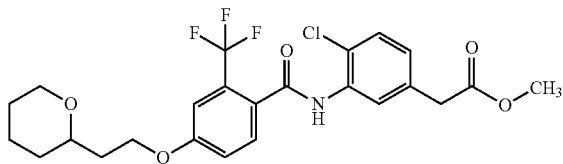

Cyanomethylene triphenylphosphine (0.507 mL) was added to a toluene (5 mL) solution of the compound (500 mg) produced in Reference Example 4, 2-(tetrahydropyran-2-yl)ethanol (CAS. No. 38786-79-7, 218 mg), and the mixture was stirred overnight at 60° C. The reaction solution was concentrated under reduced pressure, then the obtained residue was purified by silica gel column chromatography (hexane:ethyl acetate=3:1) to obtain a title compound (564 mg) having following physical property values.

HPLC Retention time (min): 1.15;

$^1$H-NMR (CDCl$_3$): δ 1.37, 1.47-1.68, 1.86, 1.94, 3.40-3.53, 3.67, 3.72, 3.98, 4.13, 4.20, 7.04, 7.13, 7.29, 7.36, 7.62, 7.93, 8.47.

Example 2: (4-Chloro-3-{4-[2-(oxan-2-yl)ethoxy]-2-(trifluoromethyl)benzamide}phenyl)acetic Acid

[Chemical 36]

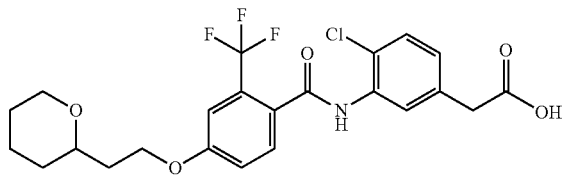

A 2 mol/L lithium hydroxide aqueous solution (0.12 mL) was added to a dimethoxyethane (0.4 mL) solution of the compound (40.0 mg) produced in Example 1, and the mixture was stirred at room temperature for 1 hour. After adding 1 mol/L hydrochloric acid to the reaction mixture, the mixture was extracted with ethyl acetate. The organic layer was washed with water and saturated saline solution, dried over sodium sulfate, and then concentrated under reduced pressure to obtain a title compound (29 mg) having following physical property values.

HPLC Retention time (min): 1.03;

$^1$H-NMR (DMSO-d$_6$): δ 1.25, 1.41-1.53, 1.63, 1.77, 1.83-1.89, 3.45, 3.63, 3.88, 4.14-4.23, 7.19, 7.32, 7.35, 7.48, 7.51, 7.68, 10.14, 12.46.

Examples 2-1 to 2-3

The same operations as in Example 1→Example 2 were carried out using a corresponding alcohol form instead of 2-(tetrahydro-2H-pyran-2-yl)ethanol, to obtain title compounds having following physical property values.

Example 2-1: {4-Chloro-3-[4-(2-cyclohexylethoxy)-2-(trifluoromethyl)benzamide]phenyl}acetic Acid

[Chemical 37]

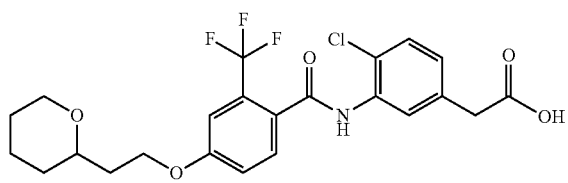

TLC: Rf 0.60 (ethyl acetate:methanol=9:1);

$^1$H-NMR (CDCl$_3$): δ 0.85-1.10, 1.13-1.35, 1.52, 1.63-1.83, 3.71, 4.08, 7.05, 7.10, 7.38, 7.62, 7.94, 8.49.

Example 2-2: {4-Chloro-3-[4-(2-phenylethoxy)-2-(trifluoromethyl)benzamide]phenyl}acetic Acid

[Chemical 38]

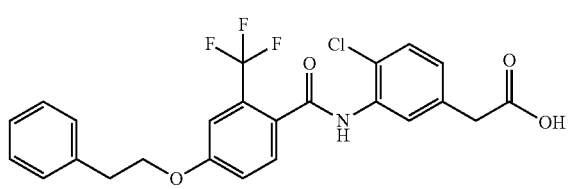

HPLC Retention time (min): 1.07;

$^1$H-NMR (DMSO-d$_6$): δ 3.09, 3.63, 4.36, 7.18, 7.24, 7.31-7.37, 7.48, 7.51, 7.68, 10.14, 12.45.

Example 2-3: {4-Chloro-3-[4-(2-cyclopropylethoxy)-2-(trifluoromethyl)benzamide]phenyl}acetic Acid

[Chemical 39]

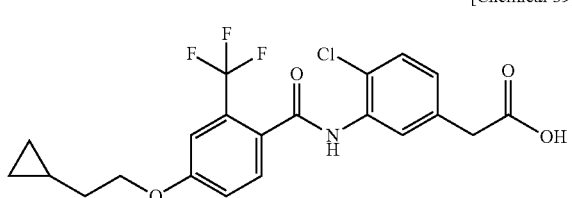

HPLC Retention time (min): 1.05;

$^1$H-NMR (DMSO-d$_6$): δ −0.02-0.01, 0.28-0.32, 0.70, 1.51, 3.48, 4.02, 7.03, 7.16, 7.20, 7.33, 7.36, 7.53, 9.99, 12.29.

Example 3: Methyl(4-chloro-3-{2,6-dimethyl-4-[2-(oxan-2-yl)ethoxy]benzamide}phenyl)acetate

[Chemical 40]

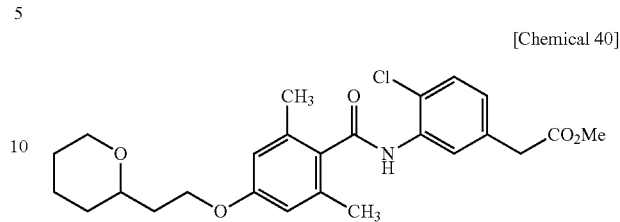

The same reaction as in Example 1 was carried out using methyl{4-chloro-3-[(4-hydroxy-2,6-dimethylbenzoyl)amino]phenyl}acetate (CAS No. 1351163-96-6, Bioorganic & Medicinal Chemistry 19 (2011) 6935-6948, Compound 44) instead of the compound produced in Reference Example 4, to obtain a title compound having following physical property values.

TLC: Rf 0.75 (hexane:ethyl acetate=1:1);

$^1$H-NMR (CDCl$_3$): δ1.33, 1.51, 1.63, 1.85, 1.91, 2.38, 3.43, 3.50, 3.68, 3.73, 3.97, 4.08, 6.63, 7.03, 7.35, 7.74, 8.49.

Example 3-1: Methyl{4-chloro-3-[4-(2-cyclohexylethoxy)-2,6-dimethylbenzamide]phenyl}acetate

[Chemical 41]

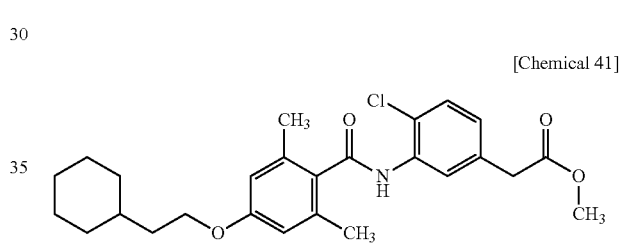

The same operation as in Example 1 was carried out using methyl{4-chloro-3-[(4-hydroxy-2,6-dimethylbenzoyl)amino]phenyl}acetate instead of the compound produced in Reference Example 4, and using 2-cyclohexylethanol (CAS No. 28438-52-0) instead of 2-(tetrahydro-2H-pyran-2-yl)ethanol, to obtain a title compound having following physical property values.

TLC: Rf 0.68 (ethyl acetate:hexane=2:1);

$^1$H-NMR (CDCl$_3$): δ0.80-1.05, 1.10-1.35, 1.40-1.55, 1.65-1.80, 2.35, 3.53, 3.68, 3.73, 4.00, 4.19, 6.61, 7.04, 7.36, 7.74, 8.50.

Example 4: (4-Chloro-3-{2,6-dimethyl-4-[2-(oxan-2-yl)ethoxy]benzamide}phenyl)acetic Acid

[Chemical 42]

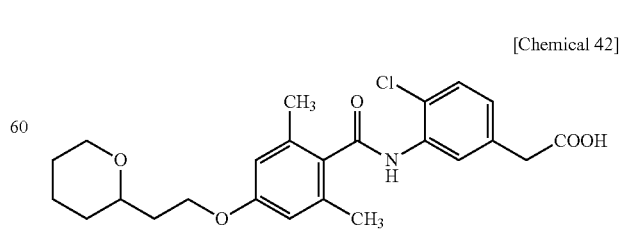

The same reaction as in Example 2 was carried out using the compound produced in Example 3 instead of the compound produced in Example 1, to obtain a title compound having following physical property values.

HPLC Retention time (min): 1.02;
$^1$H-NMR (DMSO-d$_6$): δ 1.16-1.83, 2.32, 3.39, 3.61, 3.86, 4.02, 6.66, 7.15, 7.45, 7.49, 9.95, 12.44.

Examples 4-1 to 4-2

The same operations as in Example 1→Example 2 were carried out using a corresponding alcohol form instead of 2-(tetrahydro-2H-pyran-2-yl)ethanol, and using methyl{4-chloro-3-[(4-hydroxy-2,6-dimethylbenzoyl)amino] phenyl}acetate instead of the compound produced in Reference Example 4, to obtain title compounds having following physical property values.

Example 4-1: {4-Chloro-3-[4-(2-cyclohexylethoxy)-2,6-dimethylbenzamide]phenyl}acetic Acid

[Chemical 43]

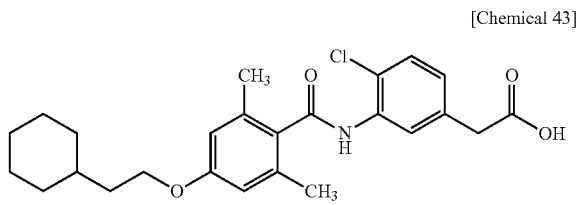 [SMILES: Cc1cc(OCCC2CCCCC2)cc(C)c1C(=O)Nc1cc(CC(=O)O)ccc1Cl]

TLC: Rf 0.27 (hexane:ethyl acetate=1:2);
$^1$H-NMR (CD$_3$OD): δ 0.83-1.08, 1.13-1.38, 1.42-1.59, 1.60-1.91, 2.41, 3.64, 4.01, 6.65, 7.19, 7.43, 7.72.

Example 4-2: {4-Chloro-3-[4-(2-cyclopropylethoxy)-2,6-dimethylbenzamide]phenyl}acetic Acid

[Chemical 44]

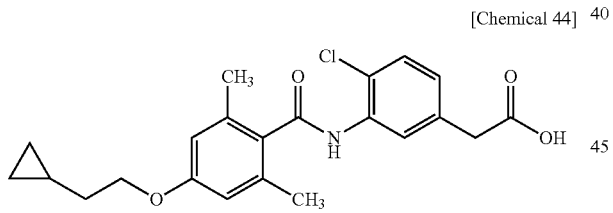

HPLC Retention time (min): 1.05;
MS(ESI, Pos.): 402 (M+H)$^+$;

Example 5: (3-{4-[(2,3-Dihydro-1H-inden-2-yl)oxy]-2,6-dimethylbenzamide}-4-fluorophenyl)acetic Acid

[Chemical 45]

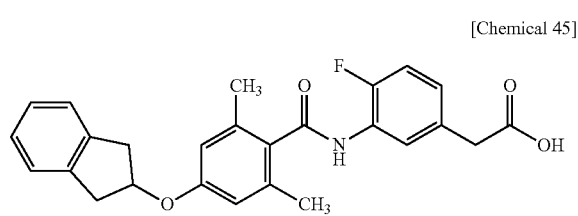 [SMILES: Cc1cc(OC2Cc3ccccc3C2)cc(C)c1C(=O)Nc1cc(CC(=O)O)ccc1F]

The same operations as in Reference Example 1→Reference Example 2→Reference Example 3→Reference Example 4→Example 1→Example 2 were carried out using methyl 2-(3-amino-4-fluorophenyl)acetate (CAS No. 257632-77-2) instead of methyl 2-(3-amino-4-chlorophenyl)acetate, using 4-hydroxy-2,6-dimethylbenzoic acid (CAS No. 75056-97-2) instead of 4-hydroxy-2-(trifluoromethyl)benzoic acid, and using 2-indanol (CAS No. 4254-29-9) instead of 2-(tetrahydro-2H-pyran-2-yl)ethanol, to obtain a title compound having following physical property values.

HPLC Retention time (min): 1.02;
$^1$H-NMR (DMSO-d$_6$): δ 2.29, 3.02, 3.39, 3.60, 5.27, 6.70, 7.13-7.28, 7.57, 10.07, 12.38.

Reference Example 5: Methyl(4-chloro-3-(2,6-dimethyl-4-[(trifluoromethanesulfonyl)oxy]benzamide}phenyl)acetate Triethylamine (0.52 mL) and N,N-bis(trifluoromethylsulfonyl)aniline (1.23 g) were added to a dichloromethane (15 mL) solution of methyl[4-chloro-3-(4-hydroxy-2,6-dimethylbenzamide)phenyl]acetate (1.00 g), and the mixture was stirred at room temperature for 4 hours. Water was added to the reaction mixture, and the mixture was extracted with ethyl acetate. The organic layer was washed with water and saturated saline solution, dried over sodium sulfate, and then concentrated under reduced pressure. The obtained residue was purified by silica gel column chromatography (hexane:ethyl acetate=10:0→7:3) to obtain a title compound (1.38 g) having following physical property values.

TLC: Rf 0.39 (hexane:ethyl acetate=2:1);
$^1$H-NMR (CDCl$_3$): δ 1.55, 2.45, 3.69, 3.73, 7.02, 7.08, 7.37, 7.40, 7.73, 8.43.

Example 6: Methyl{4-chloro-3-[4-(3-cyclohexylprop-1-yn-1-yl)-2,6-dimethylbenzamide]phenyl}acetate

[Chemical 46]

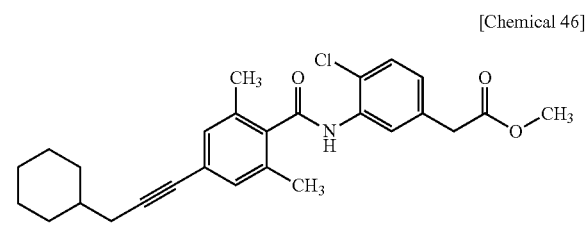 [SMILES: COC(=O)Cc1ccc(Cl)c(NC(=O)c2c(C)cc(C#CCC3CCCCC3)cc2C)c1]

3-Cyclohexyl-1-propyne (1.26 mL) and triethylamine (8.1 mL) were added to a N,N-dimethylformamide (12 mL) solution of the compound (1.38 g) produced in Reference Example 5, and the atmosphere was changed to an argon atmosphere. Copper iodide (55 mg) and bis(triphenylphosphine)palladium(II) dichloride (204 mg) were added thereto, and the mixture was stirred overnight at 50° C. Water was added to the reaction mixture, and the mixture was extracted with a mixed solvent of ethyl acetate/hexane. The organic layer was washed with water and saturated saline solution, dried over sodium sulfate, and then concentrated under reduced pressure. The obtained residue was purified by silica gel column chromatography (hexane:ethyl acetate=10:0→7:3) to obtain a title compound (1.46 g) having following physical property values.

TLC: Rf 0.45 (hexane:ethyl acetate=4:1);
$^1$H-NMR (CDCl$_3$): δ 0.95-1.40, 1.45-1.78, 1.85-1.90, 2.30, 2.37, 3.68, 3.73, 7.05, 7.14, 7.35, 7.38, 7.71, 8.47.

Example 7: {4-Chloro-3-[4-(3-cyclohexylprop-1-yn-1-yl)-2,6-dimethylbenzamide]phenyl}acetic Acid

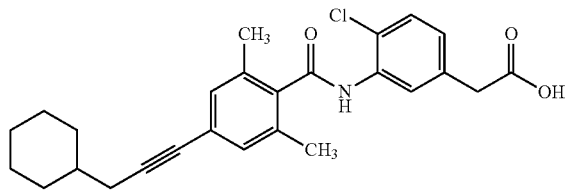

[Chemical 47]

The same operation as in Example 2 was carried out using the compound produced in Example 6 instead of the compound produced in Example 1, to obtain a title compound having following physical property values.

TLC: Rf 0.61 (ethyl acetate:methanol=9:1);

$^1$H-NMR (CDCl$_3$): 50.98-1.35, 1.56, 1.65-1.80, 1.82-1.90, 2.30, 2.38, 3.72, 7.06, 7.14, 7.36, 7.39, 7.71, 8.48.

Example 8: (4-Chloro-3-{4-[(1E)-3-cyclohexylprop-1-en-1-yl]-2,6-dimethylbenzamide}phenyl)acetic Acid

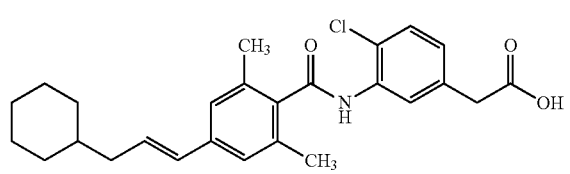

[Chemical 48]

2-[(E)-3-Cyclohexylpropene-3-yl]-4,4,5,5-tetramethyl-1,3,2-dioxaborolane (626 mg), potassium phosphate (884 mg), and [1,1'-bis(diphenylphosphino)ferrocene]palladium(II) dichloride dichloromethane adduct were added to a dioxane (12 mL) solution of the compound (1000 mg) produced in Reference Example 5, and the mixture was stirred at 50° C. for 18 hours. Water and ethyl acetate were added to the reaction mixture, then the mixture was filtered through Celite (trade name). The filtrate was extracted with ethyl acetate, the organic layer was washed with water and saturated saline solution, dried over sodium sulfate, and then concentrated under reduced pressure. The obtained residue was purified by silica gel column chromatography to obtain a methyl ester compound (533 mg) of a title compound. Using the obtained methyl ester compound, the same operation as in Example 2 was carried out to obtain a title compound having following physical property values.

TLC: Rf 0.38 (hexane:ethyl acetate:acetic acid=14:5:1);

HPLC Retention time (min): 1.31;

MS(ESI, Pos.): 440 (M+H)$^+$.

Example 9: Methyl[4-chloro-3-({2,6-dimethyl-4-[2-(oxan-2-yl)ethoxy]benzene-1-carbothioyl}amino)phenyl]acetate

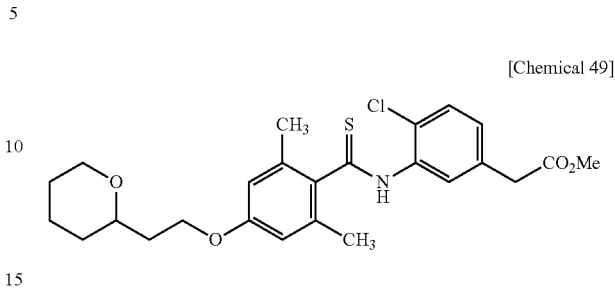

[Chemical 49]

Lawesson's reagent (CAS No. 19172-47-5, 21 mg) was added to a toluene (0.4 mL) solution of the compound (40 mg) produced in Example 3, and the mixture was stirred at 100° C. for 24 hours. The reaction mixture was concentrated under reduced pressure, and the obtained residue was purified by silica gel column chromatography (hexane:ethyl acetate=20:1→4:1) to obtain a title compound (40 mg) having following physical property values.

TLC: Rf 0.50 (hexane:ethyl acetate=2:1);

$^1$H-NMR (DMSO-d$_6$): δ 1.25, 1.46, 1.62, 1.81, 2.37, 3.44, 3.64, 3.80, 3.87, 4.02, 6.68, 7.30, 7.42, 7.55, 11.74.

Example 10: [4-Chloro-3-({2,6-dimethyl-4-[2-(oxan-2-yl)ethoxy]benzene-1-carbothioyl}amino)phenyl]acetic Acid

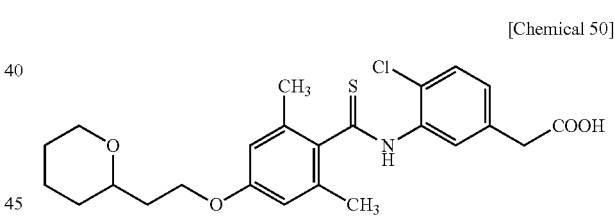

[Chemical 50]

The same operation as in Example 2 was carried out using the compound produced in Example 9 instead of the compound produced in Example 1, to obtain a title compound having following physical property values.

TLC: Rf 0.28 (dichloromethane:methanol=9:1);

$^1$H-NMR (DMSO-d$_6$): δ 1.25, 1.47, 1.62, 1.80, 2.37, 3.42, 3.67, 3.87, 4.04, 6.68, 7.29, 7.39, 7.54, 11.74, 12.46.

Examples 10-1 to 10-5

The same operations as in Example 9→Example 2 were carried out using the compounds produced in Example 1 and Example 3-1 and methyl ester compounds of the compounds produced in Examples 2-1 to 2-3 instead of the compound produced in Example 3, to obtain title compounds having following physical property values.

Example 10-1: (4-Chloro-3-{[4-(2-cyclohexy-lethoxy)-2,6-dimethylbenzene-1-carbothioyl]amino}phenyl)acetic Acid

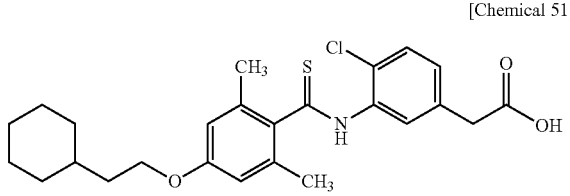

[Chemical 51]

TLC: Rf 0.46 (ethyl acetate:methanol=9:1);

$^1$H-NMR (DMSO-d$_6$): δ 0.85-1.02, 1.10-1.30, 1.43, 1.55-1.75, 2.35, 3.65, 3.99, 6.67, 7.28, 7.36, 7.51, 7.54, 11.71, 12.44.

Example 10-2: [4-Chloro-3-({4-[2-(oxan-2-yl)ethoxy]-2-(trifluoromethyl)benzene-1-carbothioyl}amino)phenyl]acetic Acid

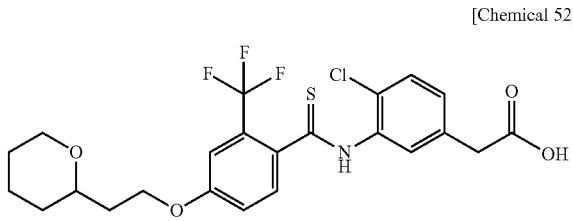

[Chemical 52]

HPLC Retention time (min): 1.05;

$^1$H-NMR (DMSO-d$_6$): δ 1.25, 1.42-1.51, 1.63, 1.77, 1.83-1.89, 3.45, 3.67, 3.88, 4.12-4.21, 7.25, 7.29-7.32, 7.35, 7.47, 7.55, 11.90, 12.46.

Example 10-3: (4-Chloro-3-{[4-(2-cyclohexy-lethoxy)-2-(trifluoromethyl)benzene-1-carbothioyl]amino}phenyl)acetic Acid

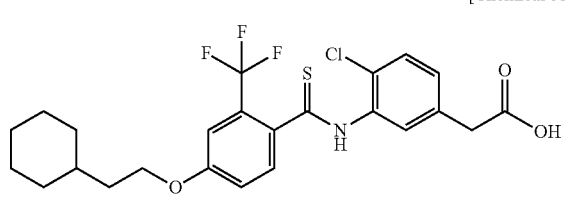

[Chemical 53]

HPLC Retention time (min): 1.21;

$^1$H-NMR (DMSO-d$_6$): δ 0.92-1.02, 1.13-1.29, 1.49, 1.63-1.77, 3.66, 4.14, 7.24, 7.29-7.32, 7.34, 7.46, 7.54, 11.89, 12.46.

Example 10-4: (4-Chloro-3-{[4-(2-phenylethoxy)-2-(trifluoromethyl)benzene-1-carbothioyl]amino}phenyl)acetic Acid

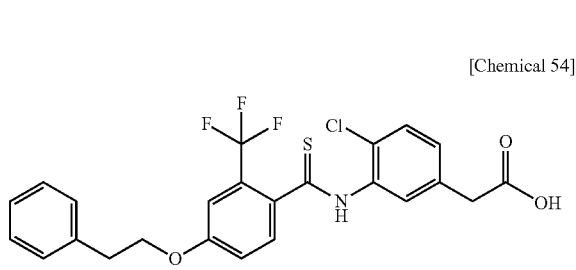 [SMILES: O=C(O)Cc1ccc(Cl)c(NC(=S)c2ccc(OCCc3ccccc3)cc2C(F)(F)F)c1]

[Chemical 54]

HPLC Retention time (min): 1.09;

$^1$H-NMR (DMSO-d$_6$): δ 3.08, 3.66, 4.34, 7.23-7.27, 7.29-7.37, 7.46, 7.55, 11.90, 12.50.

Example 10-5: (4-Chloro-3-{[4-(2-cyclopropyl-ethoxy)-2-(trifluoromethyl)benzene 1-carbothioyl]amino}phenyl)acetic Acid

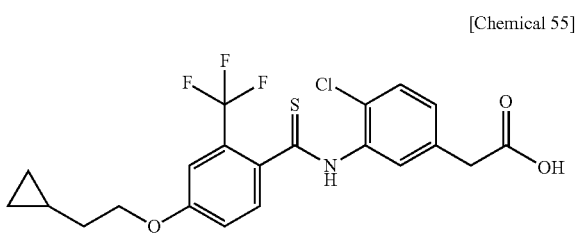 [SMILES: O=C(O)Cc1ccc(Cl)c(NC(=S)c2ccc(OCCC3CC3)cc2C(F)(F)F)c1]

[Chemical 55]

HPLC Retention time (min): 1.06;

$^1$H-NMR (DMSO-d$_6$): δ −0.02-0.01, 0.28-0.32, 0.70, 1.51, 3.50, 4.00, 7.08, 7.13-7.18, 7.31, 7.38, 11.74, 12.30.

Example 11

Using the compound produced in Example 9, optical resolution was performed by supercritical fluid chromatography (SFC) to obtain a title compound having following physical property values.

Example 11-1: Methyl{4-chloro-3-[(2,6-dimethyl-4-{2-[(2R)-oxan-2-yl]ethoxy}benzene-1-carbothioyl)amino]phenyl}acetate

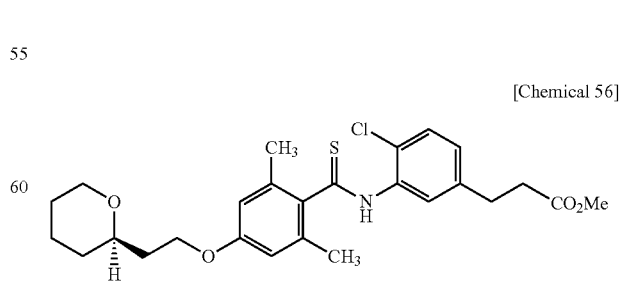

[Chemical 56]

HPLC Retention time (min): 13.2 (CHIRAL PAK IC, hexane: isopropanol=70:30);

Example 11-2: Methyl{4-chloro-3-[(2,6-dimethyl-4-{2-[(2S)-oxan-2-yl]ethoxy}benzene-1-carbothioyl)amino]phenyl}acetate

[Chemical 57]

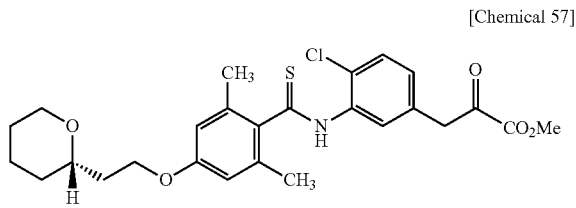 [SMILES: COC(=O)C(=O)Cc1ccc(Cl)c(NC(=S)c2c(C)cc(OCC[C@@H]3CCCCO3)cc2C)c1]

HPLC Retention time (min): 11.8 (CHIRAL PAK IC, hexane: isopropanol=70:30);

Example 12: {4-Chloro-3-[(2,6-dimethyl-4-{2-[(2R)-oxan-2-yl]ethoxy}benzene-1-carbothioyl]amino}phenyl}acetic Acid

[Chemical 58]

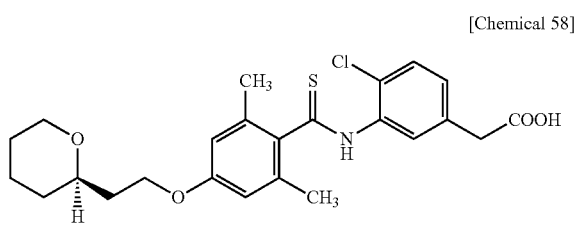 [SMILES: Cc1cc(OCC[C@H]2CCCCO2)cc(C)c1C(=S)Nc1cc(CC(=O)O)ccc1Cl]

The same operation as in Example 2 was carried out using the compound produced in Example 11-1 instead of the compound produced in Example 1, to obtain a title compound having following physical property values.
TLC: Rf 0.28 (dichloromethane:methanol=9:1);
HPLC Retention time (min): 1.05;
MS(ESI, Pos.): 462 (M+H)$^+$;
$^1$H-NMR (DMSO-d$_6$): δ 1.25, 1.47, 1.62, 1.80, 2.37, 3.42, 3.67, 3.87, 4.04, 6.68, 7.29, 7.39, 7.54, 11.74, 12.46.

Example 13: (4-Chloro-3-[(2,6-dimethyl-4-{2-[(2S)-oxan-2-yl]ethoxy}benzene-1-carbothioyl)amino]phenyl}acetic Acid

[Chemical 59]

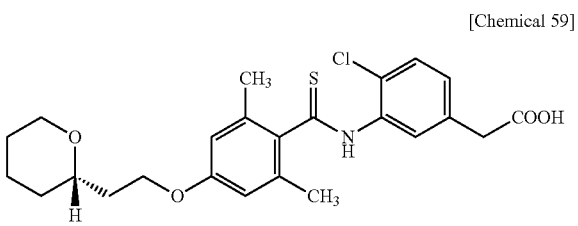 [SMILES: Cc1cc(OCC[C@@H]2CCCCO2)cc(C)c1C(=S)Nc1cc(CC(=O)O)ccc1Cl]

The same operation as in Example 2 was carried out using the compound produced in Example 11-2 instead of the compound produced in Example 1, to obtain a title compound having following physical property values.
TLC: Rf 0.28 (dichloromethane:methanol=9:1);
HPLC Retention time (min): 1.05;
MS(ESI, Pos.): 462 (M+H)$^+$;
$^1$H-NMR (DMSO-d$_6$): δ 1.25, 1.47, 1.62, 1.80, 2.37, 3.42, 3.67, 3.87, 4.04, 6.68, 7.29, 7.39, 7.54, 11.74, 12.46.

Reference Example 6: Methyl 2-(3-amino-4-fluorophenyl)propanoate

An acetic acid (5 mL) solution of methyl 2-(4-fluoro)-3-nitrophenyl)propanoate (CAS No. 1428790-43-5, 3.9 g) produced by a method described in WO 2013/045451 A was added to a mixture obtained by adding iron powder (4.8 g) to acetic acid (34 mL) and water (4.0 mL) and heating to 65° C., and the reaction mixture was stirred at 65° C. for 30 minutes. The reaction mixture was cooled to room temperature and then filtered through Celite (trade name), and the filtrate was cooled to 0° C. Thereafter, a 2 N aqueous sodium hydroxide solution (345 mL) was poured thereto, and the mixture was filtered through Celite (trade name) again. The filtrate was extracted twice with tert-butyl methyl ether, and the organic layer was washed with saturated saline solution, dried over anhydrous magnesium sulfate, and then concentrated under reduced pressure. The obtained residue was purified by silica gel column chromatography (hexane:ethyl acetate=99:1→65:35) to obtain a title compound (3.4 g) having following physical property values.
$^1$H-NMR (CDCl$_3$): δ 1.45, 3.60, 3.63, 3.71, 6.60, 6.73, 6.91.

Example 14: 2-{3-[({2,6-Dimethyl-4-[2-(tetrahydro-2H-pyran-2-yl)ethoxy]phenyl}carbothioyl)amino]-4-fluorophenyl}propanoic Acid

[Chemical 60]

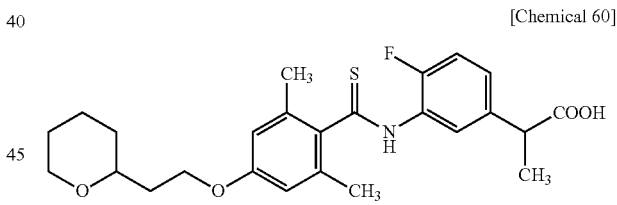

The same operations as in Reference Example 2→Reference Example 3→Reference Example 4→Example 1→Example 9→Example 2 were carried out using the compound produced in Reference Example 6 instead of methyl 2-(3-amino-4-chlorophenyl)acetate, and 4-acetoxy-2,6-dimethylbenzoic acid (CAS No. 1351163-93-3) produced by a method described in Bioorganic & Medicinal Chemistry, vol. 19, 6935-6948, 2011 instead of the compound produced in Reference Example 1, to obtain a title compound having following physical property values.
HPLC Retention time (min): 1.07;
MS(ESI, Pos., 20V): 460 (M+H)$^+$;
$^1$H-NMR (DMSO-d$_6$): δ 1.18, 1.19-1.29, 1.38, 1.39-1.55, 1.62, 1.71-1.87, 2.32, 3.26-3.52, 3.77, 3.87, 4.04, 6.69, 7.26-7.43, 11.64, 12.44.

Example 15: 1-{3-[({2,6-Dimethyl-4-[2-(tetrahydro-2H-pyran-2-yl)ethoxy]phenyl}carbothioyl)amino]-4-fluorophenyl}cyclopropane Carboxylic Acid

[Chemical 61]

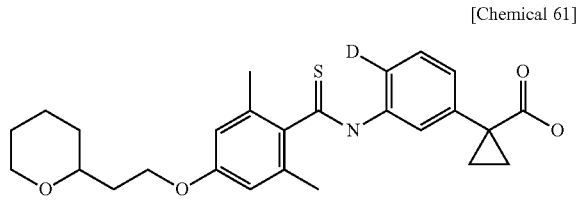 [SMILES: [2H]c1ccc(C2(C(=O)O)CC2)cc1NC(=S)c1c(C)cc(OCCC2CCCCO2)cc1C]

The same operations as in Reference Example 6→Reference Example 2→Reference Example 3→Reference Example 4→Example 1→Example 9→Example 2 were carried out using methyl 1-(4-fluoro-3-nitrophenyl)cyclopropane-1-carboxylate (CAS No., 2260554-65-0) produced by a method described in WO 2019/003143 A, and 4-acetoxy-2,6-dimethylbenzoic acid instead of the compound produced in Reference Example 1, to obtain a title compound having following physical property values.

HPLC Retention time (min): 1.09;

MS(ESI, Pos., 20V): 472 (M+H)$^+$;

$^1$H-NMR (DMSO-$d_6$): δ 1.12-1.31, 1.38-1.54, 1.61, 1.71-1.86, 2.32, 3.27-3.47, 3.87, 4.03, 6.68, 7.26, 7.36, 7.43, 11.64, 12.42.

Example 16: Methyl 2-[4-chloro-3-({2,6-dimethyl-4-[2-(oxan-2-yl)ethoxy]benzene-1-carbothioyl}amino)phenyl]-2-methylpropanoate

[Chemical 62]

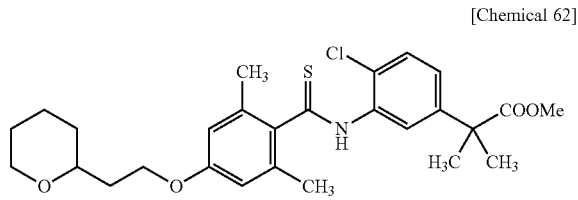 [SMILES: COC(=O)C(C)(C)c1ccc(Cl)c(NC(=S)c2c(C)cc(OCCC3CCCCO3)cc2C)c1]

The same operations as in Reference Example 2→Reference Example 3→Reference Example 4→Example 1→Example 9 were carried out using methyl 2-(3-amino-4-chlorophenyl)-2-methylpropanoate (CAS No. 343326-75-0) produced by the method described in Bioorganic Medicinal Chemistry, 2011, vol. 19, 6935-6948, and 4-acetoxy-2,6-dimethylbenzoic acid instead of the compound produced in Reference Example 1, to obtain a title compound having following physical property values.

$^1$H-NMR (DMSO-$d_6$): δ1.20-1.28, 1.42-1.50, 1.53, 1.58-1.65, 1.72-1.85, 2.36, 3.28-3.48, 3.61, 3.85-3.90, 4.00-4.08, 6.68, 7.35, 7.43, 7.58 11.75.

Example 17: 2-{4-Chloro-3-[({2,6-dimethyl-4-[2-(tetrahydro-2H-pyran-2-yl)ethoxy]phenyl}carbothioyl)amino]phenyl}-2-methylpropanoic Acid

[Chemical 63]

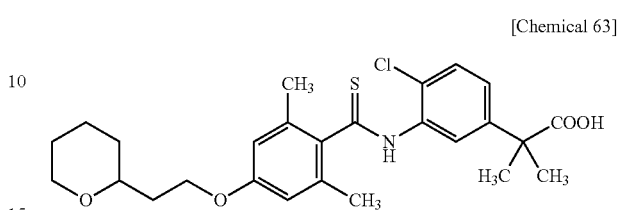

Using the compound produced in Example 16, the same operation as in Example 2 was carried out to obtain a title compound having following physical property values.

HPLC Retention time (min): 1.14;

MS(ESI, Pos., 20V): 490 (M+H)$^+$;

$^1$H-NMR (DMSO-$d_6$): δ1.20-1.25, 1.43-1.49, 1.49, 1.58-1.65, 2.36, 3.26-3.48, 3.77, 4.00-4.08, 6.68, 7.38, 7.46, 7.58 11.74, 12.57.

Example 18: Methyl 2-{4-chloro-3-[(2,6-dimethyl-4-{2-[(2S)-oxan-2-yl]ethoxy}benzene-1-carbothioy)amino]phenyl}-2-methylpropanoate, and methyl 2-{4-chloro-3-[(2,6-dimethyl-4-{2-[(2R)-oxan-2-yl]ethoxy}benzene-1-carbothioyl)amino]phenyl}-2-methylpropanoate Using the compound produced in Example 16, optical resolution was performed by supercritical fluid chromatography (SFC) to obtain a title compound having following physical property values.

Separation conditions Column: CHIRALPAK IC 5 μm 20 mm×250 (manufactured by Daicel Corporation); CO$_2$: (ethyl acetate/methanol=9/1)=78/22

Example 18-1: (First Peak)

SFC Retention time (min): 3.69 (CHIRALPAK IC 5 μm 20 mm×250 (manufactured by Daicel Corporation); CO$_2$: (ethyl acetate/methanol=9:1)=78:22)

Example 18-2: (Second Peak)

SFC Retention time (min): 5.32 (CHIRALPAK IC 5 μm 20 mm×250 (manufactured by Daicel Corporation); CO$_2$: (ethyl acetate/methanol=9:1)=78:22)

Example 19: 2-{4-Chloro-3-[(2,6-dimethyl-4-{2-[(2S)-oxan-2-yl]ethoxy}benzene-1-carbothioyl)amino]phenyl}-2-methylpropanoic Acid, and 2-{4-chloro-3-[(2,6-dimethyl-4-{2-[(2R)-oxan-2-yl]ethoxy}benzene-1-carbothioyl)amino]phenyl}-2-methylpropanoic Acid Using the compound obtained in Example 18-1 or Example 18-2, the same operation as in Example 2 was carried out to obtain a title compound having following physical property values.

Example 19-1: (Compound Produced Using Compound Produced in Example 18-1)

HPLC Retention time (min): 1.14;
MS(ESI, Pos., 20V): 490 (M+H)$^+$;
$^1$H-NMR (DMSO-d$_6$): δ1.20-1.25, 1.43-1.49, 1.49, 1.58-1.65, 2.36, 3.26-3.48, 3.77, 4.00-4.08, 6.68, 7.38, 7.46, 7.58 11.74, 12.57.

Example 19-2: (Compound Produced Using Compound Produced in Example 18-2)

HPLC Retention time (min): 1.14;
MS(ESI, Pos., 20V): 490 (M+H)$^+$;
$^1$H-NMR (DMSO-d$_6$): δ1.20-1.25, 1.43-1.49, 1.49, 1.58-1.65, 2.36, 3.26-3.48, 3.77, 4.00-4.08, 6.68, 7.38, 7.46, 7.58 11.74, 12.57.

Example 20: 2-{3-[({2,6-Dimethyl-4-[2-(tetrahydro-2H-pyran-2-yl)ethoxy]phenyl}carbothioyl)amino]-4-fluorophenyl}-2-methylpropanoic Acid

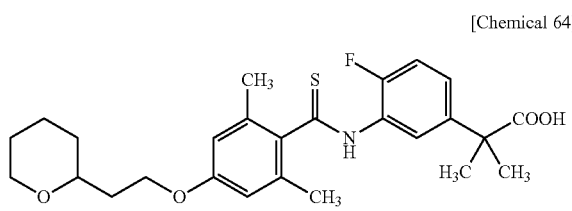

[Chemical 64]

The same operations as in Reference Example 6→Reference Example 2→Reference Example 3→Reference Example 4→Example 1→Example 9→Example 2 were carried out using methyl 2-(4-fluoro-3-nitrophenyl)-2-methylpropanoate produced by a method described in WO 2018/116107 A, and 4-acetoxy-2,6-dimethylbenzoic acid instead of the compound produced in Reference Example 1, to obtain a title compound having following physical property values.

HPLC Retention time (min): 1.09;
MS(ESI, Pos., 20V): 474 (M+H)$^+$;
$^1$H-NMR (DMSO-d$_6$): δ 1.25, 1.41-1.48, 1.49, 1.62, 1.71-1.85, 2.31, 3.32, 3.43, 3.87, 3.99-4.08, 6.68, 7.31, 7.38, 7.44, 11.65, 12.51.

Example 21: 2-(4-Chloro-3-{[(2,6-dimethyl-4-{2-[(2R)-tetrahydro-2H-pyran-2-yl]ethoxy}phenyl)carbothioyl]amino}phenyl)propanoic Acid

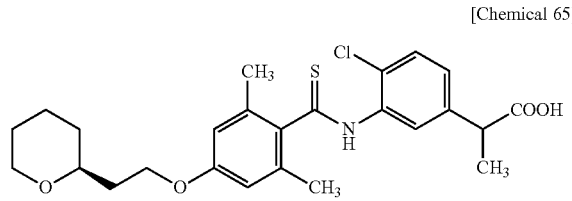

[Chemical 65]

DIPEA (2.2 mL) and methoxymethyl chloride (0.57 mL) were added to a dichloromethane (25 mL) solution of the compound (1200 mg) produced in Example 11-1 at 0° C., and the reaction mixture was stirred at room temperature for 1 hour. The reaction solution was purified by silica gel column chromatography (hexane:ethyl acetate=95:5→35:65) to obtain a crude product (1300 mg). Cesium carbonate (4.1 g) and methyl iodide (0.78 mL) were added to a dimethylacetamide (10 mL) solution of the crude product, and the reaction mixture was stirred at 35° C. for 16 hours. The reaction mixture was cooled to room temperature, and then an aqueous ammonium chloride solution was poured thereto. The mixture was extracted twice with tert-butyl methyl ether, and the organic layer was washed with saturated saline solution, dried over anhydrous sodium sulfate, and then concentrated under reduced pressure. The obtained residue was purified by silica gel column chromatography (hexane:ethyl acetate=90:10→0:100) to obtain a crude product (410 mg). A 5 mol/L hydrochloric acid aqueous solution (5 mL) was added to a dioxane (10 mL) solution of the crude product, and the reaction mixture was stirred at room temperature for 1 hour. The reaction mixture was extracted twice with tert-butyl methyl ether, and the organic layer was washed with saturated saline solution, dried over anhydrous sodium sulfate, and then concentrated under reduced pressure. The obtained residue was purified by silica gel column chromatography (hexane:ethyl acetate=90:10→0:100) to obtain a crude product (320 mg). Methanol (4 mL) and a 2 mol/L sodium hydroxide aqueous solution (4 mL) were added to a tetrahydrofuran (4 mL) solution of the crude product, and the reaction mixture was stirred at room temperature for 3 hours. A 2 mol/L hydrochloric acid aqueous solution was added to the reaction mixture, the mixture was extracted twice with tert-butyl methyl ether, and the organic layer was washed with saturated saline solution, dried over anhydrous sodium sulfate, and then concentrated under reduced pressure. The obtained residue was purified by silica gel column chromatography (hexane:ethyl acetate=90:10→0:100) to obtain a title compound (275 mg) having following physical property values.

HPLC Retention time (min): 1.10;
MS(ESI, Pos., 20V): 476 (M+H)$^+$;
$^1$H-NMR (CDCl$_3$): δ 0.78-0.84, 1.30-1.90, 2.17-2.25, 2.39, 3.39-3.60, 3.90-4.12, 4.54, 6.37, 6.52-6.65, 7.01-7.04, 7.25-7.30, 7.42-7.45, 8.71, 8.88, 9.70.

Example 22: [4-Chloro-3-({[4-(2-cyclohexylethoxy)-2,6-dimethylphenyl]carbothioyl}amino)phenyl] sodium Acetate

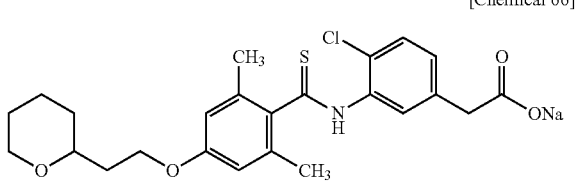

[Chemical 66]

A 1 mol/L sodium hydroxide aqueous solution (0.13 mL) was added to a dioxane (2 mL) solution of the compound (60 mg) produced in Example 10-1 and then the mixture was freeze-dried to obtain a title compound (49 mg) having following physical property values.

HPLC Retention time (min): 1.38;
MS(ESI, Pos., 20V): 460 (M+H-Na)$^+$;
$^1$H-NMR (DMSO-d$_6$): δ 0.87-1.02, 1.10-1.28, 1.47, 1.67-1.79, 2.36, 3.26, 3.99, 6.65, 7.12-7.28, 7.38, 11.70.

Pharmacological Examples

Biological Example 1: Measurement of DP Receptor Antagonistic Activity Using Human DP Receptor Expressing Cells cAMP-HTRF kit (SCETI MEDICAL LABO K.K., 62AM6PEJ) was used to measure DP receptor antagonistic activity. To a 384 well plate was added 10 µL/well of the compound of the present invention prepared at various concentrations and prostaglandin D2 (final concentration 10 nmol/L). Human DP receptor-expressing cells were suspended in phosphate buffer containing 2 µmoL/L diclofenac and 1 mmol/L IBMX (3-isobutyl-1-methylxantine) and seeded to 5000 cells/10 µL/well. After cell seeding, the cells were incubated at room temperature for 1 hour. Thereafter, anti-cAMP Cryptate conjugate and a cAMP-d2 solution were added according to a method of the measurement kit, and the mixture was incubated at room temperature for 1 hour, then the cAMP concentration in the sample was quantified.

Intensity of DP receptor antagonistic action by the compound of the present invention was represented by $IC_{50}$ value (concentration of the compound of the present invention required to inhibit 50% of cAMP production in the absence of the compound of the present invention) calculated from an inhibition ratio to the cAMP production increased by 10 nmol/L prostaglandin D2 stimulation. Table 1 shows the DP receptor antagonistic activity of the compounds of the present invention.

TABLE 1

| Example number | DP Antagonistic activity $IC_{50}$ (µm) |
| --- | --- |
| 2-1 | 0.034 |
| 4 | 0.058 |
| 4-1 | 0.011 |
| 5 | 0.010 |
| 7 | 0.016 |
| 8 | 0.0037 |
| 10 | 0.0096 |
| 10-1 | 0.0017 |
| 10-4 | 0.0051 |
| 12 | 0.0048 |
| 20 | 0.035 |
| 21 | 0.0078 |

The compounds of the present invention showed a strong antagonistic activity against DP receptors.

Pharmacokinetic Test 1: Measurement of Concentration of Compound of Present Invention in Cerebrospinal Fluid (Hereinbelow, CSF)

(1) CSF Collection

Five test substances were mixed, and a test substance solution was prepared so that the dose of each test substance was 3 mg/5 mL/kg. The medium used was 5% DMSO 20% kolliphor HS15/propylene glycol (7:3). The test substance solution was orally administered to male 8- to 10-week-old Wistar rats purchased from Charles River Japan. Three hours after administration, the rats were anesthetized and CSF was collected by cisternal puncture. The same amount of ethanol (wako) as CSF was taken with a syringe used for collection, and the compound adsorbed on the syringe was recovered by washing.

(2) Measurement

Candesartan (TRC) was used as an internal standard substance, 40 µL of acetonitrile and 160 µL of Candesartan-containing acetonitrile/ethanol (7:3) were added to 10 µL of the obtained CSF sample, and the mixture was stirred. To prepare a calibration curve, 40 µL of the compound solution and 160 µL of Candesartan-containing acetonitrile/ethanol (7:3) were added to 10 µL of plasma, and the mixture was stirred. The entire amount of each solution was transferred to a deproteinization filter plate and suction filtered. The obtained filtrate was appropriately diluted with acetonitrile/water (1:1) and used for measurement. In the measurement, standard samples for calibration curve were prepared in the same matrix and analyzed in the same manner. The measurement was performed under the following conditions.

Liquid Chromatography System: Prominence $UFLC_{XR}$ (Shimadzu Corporation),

Column: Shim-pack XR-ODSII 2.0 mm ID×75 mm (Shimadzu Corporation),

Column temperature: 40° C.,

Mobile phase: A: 0.2% formic acid 5 mmol/L ammonium acetate aqueous solution, B: acetonitrile, Gradient Program:

Time (Mobile phase B (%)): 0 min (10)→1.5 min (90)→3.0 min (90)→3.1 min (10)→4 min (10), Flow rate: 0.5 mL/min Mass spectrometry system: API4000, API5000 (AB SCIEX)

(3) Analysis

A regression equation was calculated from the peak area ratio (peak area of the test substance/peak area of the internal standard substance) obtained by measuring the standard samples for calibration curve using analysis software Analyst ver. 1.5.2 (AB SCIEX). The peak area ratio was also obtained for a measurement sample and substituted into the regression equation to calculate a quantitative value. In calculation of mean value and standard deviation, points below the lower limit of quantification were calculated as 0.

The results are shown in Table 2.

TABLE 2

| Example number | Compound concentration in CSF (ng/mL) |
| --- | --- |
| 4-1 | 29 |
| 7 | 45 |
| 8 | 28 |
| 10 | 43 |
| 10-1 | 36 |
| 10-2 | 55 |
| 10-4 | 34 |
| 12 | 48 |
| 20 | 52 |
| 21 | 66 |

Using the compound described in Example 13-24 in Patent Literature 2 of the prior art document as a comparative compound, the compound concentration in CSF was measured and found to be 4.8 ng/mL. The compound concentration in CSF of the compounds of the present invention was higher than that of the comparative compound, and showed good central transferability.

Biological Example 2: Effect of Prolonging Normal Rat Awakening Time

Chronic electrodes were placed in the brain and cervical muscles of rats to prepare rats in which electroencephalogram and electromyogram can be measured. After a recovery period of one week or more, the rat and a biological signal amplifier were connected in a shield box that blocked sound and electrical noise. After acclimatization in a measurement cage for 1 hour or more, various doses of the compound of the present invention were orally administered to rats in a single dose, and electroencephalogram and electromyogram were recorded 6 hours after the oral administration. After the measurement was completed, the rats were returned to a breeding cage each time, and a vehicle and each compound were evaluated with a washout period of one week or more.

The recorded electroencephalogram and electromyogram were analyzed using SleepSign Ver. 3 and divided into epochs every 10 seconds, and the stage was determined for any of awakening, non-REM sleep or REM sleep, with reference to characteristics of the electroencephalogram and electromyogram and spectral analysis results of each frequency component of the brain wave. The stage was determined as "awakening" when a high-amplitude electromyogram was observed, "non-REM sleep" when a high-amplitude slow wave and a low-amplitude electromyogram were observed, and "REM sleep" when a low-amplitude electroencephalogram including theta wave component and a low-amplitude electrocardiogram were observed. An epoch whose stage was difficult to determine due to noise and the like was based on a determination result of a previous epoch.

After determining the sleep-wake state, a difference between a total awakening time of 6 hours after administration of the compound of the present invention-administered group and a total awakening time of 6 hours after administration of the vehicle-administered group was expressed as an index of awakening time-prolonging effect.

As a result of evaluating the awakening time-prolonging effect of the compound of the present invention, for example, Example Compound 8 and Example Compound 12 showed awakening time-prolonging effects of 48 minutes and 60 minutes at a dose of 3 mg/kg, respectively, and it has been shown that the compound of the present invention is useful as a therapeutic agent for sleep-wake disorders.

Formulation Example

Typical formulation example used in the present invention is shown below.

{4-Chloro-3-[(2,6-dimethyl-4-{2-[(2R)-oxan-2-yl]ethoxy}benzene-1-carbothioyl)amino]phenyl}acetic acid (100 g), carboxymethyl cellulose calcium (20 g), magnesium stearate (10 g) and microcrystalline cellulose (870 g) are mixed by a conventional method and then compressed to obtain about 10,000 tablets containing 10 mg of active ingredient in one tablet.

INDUSTRIAL APPLICABILITY

Since the compound of the present invention has strong DP receptor antagonistic activity and excellent central transferability, it is useful as a preventive and/or therapeutic agent for DP receptor-mediated diseases, particularly, sleep-wake disorders.

The invention claimed is:

1. {4-Chloro-3-[(2,6-dimethyl-4-{2-[(2R)-oxan-2-yl]ethoxy}benzene-1-carbothioyl)amino]phenyl}acetic acid, or a pharmaceutically acceptable salt thereof.

2. A compound of the structure formula:

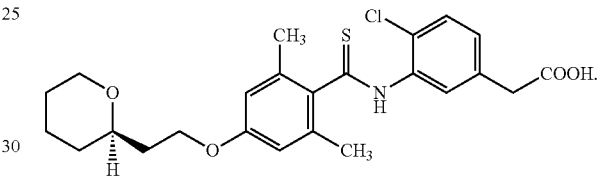

3. A pharmaceutically acceptable salt of a compound of the structural formula:

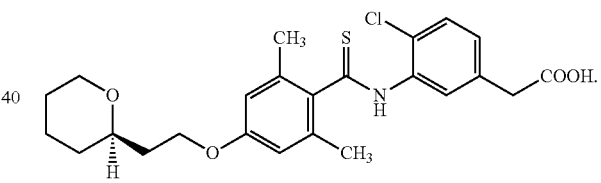

* * * * *